US008808879B2

(12) United States Patent
Mochizuki et al.

(10) Patent No.: US 8,808,879 B2
(45) Date of Patent: *Aug. 19, 2014

(54) PHOTOTHERAPY DEVICES AND METHODS COMPRISING SUBSTITUTED CARBAZOLE COMPOUNDS

(75) Inventors: Amane Mochizuki, Carlsbad, CA (US); Sazzadur Rahman Khan, San Diego, CA (US); Shijun Zheng, San Diego, CA (US); Keisaku Okada, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 171 days.

This patent is subject to a terminal disclaimer.

(21) Appl. No.: 13/183,981

(22) Filed: Jul. 15, 2011

(65) Prior Publication Data

US 2012/0016449 A1    Jan. 19, 2012

Related U.S. Application Data

(60) Provisional application No. 61/365,485, filed on Jul. 19, 2010.

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 548/304.1; 548/418; 548/440; 548/444

(58) Field of Classification Search
USPC .................. 428/690, 917; 313/504, 505, 506; 257/40, E51.05, E51.026, E51.032; 548/428, 440, 304.1, 418, 444
See application file for complete search history.

(56) References Cited

U.S. PATENT DOCUMENTS

| 8,586,205 B2 | 11/2013 | Zheng et al. | |
| 2010/0060154 A1* | 3/2010 | Nomura et al. | 313/504 |
| 2010/0179469 A1* | 7/2010 | Hammond et al. | 604/20 |

FOREIGN PATENT DOCUMENTS

| CN | 101 104 795 | 1/2008 |
| WO | WO 2005/090512 | 9/2005 |
| WO | WO 2010/021524 | 2/2010 |
| WO | WO 2010/044607 | 4/2010 |
| WO | WO 2011/034967 | 3/2011 |
| WO | WO 2012/012295 | 1/2012 |

OTHER PUBLICATIONS

Ding, et al., "Effect of Ancillary Ligands on the Properties of Heteroleptic Green Iridium Dendrimers Functionalized with Carbazole Dendrons", Journal of Organometallic Chemistry, Mar. 24, 2009, vol. 694, pp. 2700-2704.
Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-173.
Yang et al., "Efficient Flourescent Deep-Blue and Hybrid White Emitting Devices Based on Carbazole/Bensimidazole Compound", The Journal of Physical Chemistry, Jun. 7, 2011, vol. 115, pp. 14347-14352.
International Search Report and Written Opinion in PCT Application No. PCT/US2011/044261, dated Oct. 19, 2011.

* cited by examiner

*Primary Examiner* — Gregory Clark
(74) *Attorney, Agent, or Firm* — Knobbe Martens Olson & Bear LLP

(57) ABSTRACT

Methods and devices related to the treatment of diseases using phototherapy are described. Some embodiments provide an organic light-emitting diode device, such as a light-emitting device for phototherapy, comprising a compound of Formula 1. Methods of treating disease diseases with phototherapy are also described.

13 Claims, 6 Drawing Sheets

(b) Dead cell (after 25J/cm² irradiation)

(a) Healthy cell (Control)

US 8,808,879 B2

PHOTOTHERAPY DEVICES AND METHODS COMPRISING SUBSTITUTED CARBAZOLE COMPOUNDS

CROSS-REFERENCE TO RELATED APPLICATIONS

This application claims the benefit of U.S. Provisional Application No. 61/365,485, filed Jul. 19, 2010, which is incorporated by reference herein in its entirety.

BACKGROUND OF THE INVENTION

1. Field of the Invention

The embodiments relate to light-emitting devices, such as those containing organic light-emitting diodes, for uses such as phototherapy.

2. Description of the Related Art

Phototherapy may be useful in treating a number of medical conditions. However, light sources such as lasers, which may be used for phototherapy, may be expensive, difficult to transport, and not suitable for home or outpatient treatment. Therefore, there may be a need for alternative sources of light for phototherapy which may be less expensive and more portable.

SUMMARY OF THE INVENTION

Some embodiments relate to organic light-emitting devices which may be used for phototherapy. These devices typically comprise an organic light-emitting diode, such as an organic light-emitting diode comprising an anode, a cathode, and an organic light-emitting layer disposed between the anode and the cathode. In some embodiments, the organic light-emitting layer may comprise a light-emitting component, such as a fluorescent or a phosphorescent compound, which may include a substituted carbazole compound, such as a compound described herein. In some embodiments, the light-emitting layer may comprise a host compound, such as a substituted carbazole compound, including a compound described herein. Some devices may also comprise wavelength convertor.

Some embodiments provide a compound represented by Formula 1:

(Formula 1)

wherein Cb may be optionally substituted carbazole; A may be absent, or may be $Ph^2$ or $Ph^2$-$Het^2$; $Ph^1$ and $Ph^2$ may independently be optionally substituted phenyl; $Ar^1$ may be optionally substituted $C_{6-10}$ aryl; and $Het^1$ and $Het^2$ are independently optionally substituted benzimidazol-2-yl or optionally substituted benzooxazol-2-yl.

Some embodiments provide a light-emitting device for use in phototherapy comprising: a light-emitting layer comprising a compound described herein, wherein the device is configured to emit a therapeutically effective amount of light to a mammal.

In some embodiments, these devices may be used in a method of carrying out phototherapy comprising: exposing at least a portion of a tissue of a mammal to light from a device described herein. In some embodiments, the tissue comprises a photosensitive compound which may not be naturally in the tissue, and at least a portion of the photosensitive compound may be activated by exposing the portion of the tissue to light from the device.

Some embodiments provide a method of treating a disease, comprising: exposing at least a portion of a tissue of a mammal in need thereof with light from a device described herein. In some embodiments, the tissue comprises a photosensitive compound which may not naturally be in the tissue, and at least a portion of the photosensitive compound may be activated by exposing the portion of the tissue to light from the device to thereby treat the disease.

Some embodiments provide a phototherapy system comprising: a device described herein; and a photosensitive compound; wherein the photosensitive compound is suitable for administration to a tissue of a mammal in need of phototherapy; and wherein the device is configured to emit light of a wavelength which can activate at least a portion of the photosensitive compound when it is in the tissue.

These and other embodiments are described in greater detail below.

DETAILED DESCRIPTION OF THE PREFERRED EMBODIMENT

Figure 3:
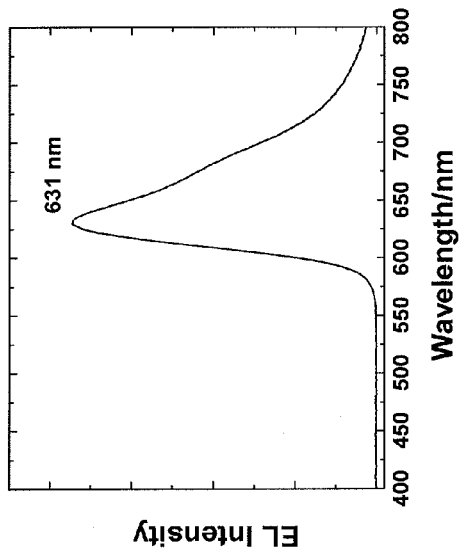
FIG. 3 is a graph depicting the electroluminescence spectrum of an embodiment of an organic light-emitting device of FIG. 2.

Unless otherwise indicated, when a chemical structural feature such as alkyl or aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of less than about 500 g/m, about 300 g/m, about 200 g/m, about 100 g/m, or about 50 g/m. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, carbazolyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

In some embodiments, the substituents include, but are not limited to, $C_{1-6}$ alkyl, $C_{1-6}$ alkenyl, $C_{1-6}$ alkynyl, carbazolyl, $C_{6-10}$ aryl, $C_{12-20}$ diarylamino, $C_{2-10}$ heteroaryl, $C_{3-6}$ heteroalicyclyl, hydroxy, $C_{1-6}$ alkoxy, $C_{1-6}$ aryloxy, $C_{1-6}$ acyl, $C_{1-6}$ ester, mercapto, $C_{1-6}$ alkylthio, $C_{1-6}$ arylthio, cyano, halogen, carbonyl, thiocarbonyl, $C_{1-6}$ O-carbamyl, $C_{1-6}$ N-carbamyl, $C_{1-6}$ O-thiocarbamyl, $C_{1-6}$ N-thiocarbamyl, $C_{1-6}$ C-amido, $C_{1-6}$ N-amido, $C_{1-6}$ S-sulfonamido, $C_{1-6}$ N-sulfonamido, C-carboxy, protected C-carboxy, O-carboxy, isocyanato, thiocyanato, isothiocyanato, nitro, $C_{1-6}$ haloalkyl, $C_{1-6}$ haloalkoxyl, and $C_{1-6}$ amino, including mono- and di-substituted amino groups, and the protected derivatives thereof.

As used herein, the term "carbazole" refers to the ring system:

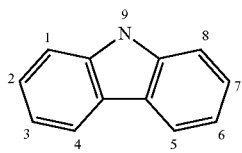

Attachment to the rest of the molecule may occur at any possible position. When optionally substituted, the addition of a substituent may occur at any possible position. The numbers may be used to refer to a position of a particular feature. For example, if A attaches at the 3-position, $Ph^1$ attaches at the 6-position, and $Ar^1$ attaches at the 9-position, a structure of Formula 2 may be obtained, wherein $R^a$, $R^b$, $R^c$, $R^d$, $R^e$, and $R^f$ may independently be H or a substituent, such as any substituent described herein.

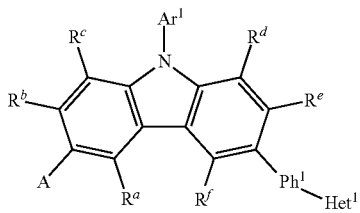

(Formula 2)

As used herein, the term "aryl" refers to an aromatic ring or ring system such as phenyl, naphthyl, etc. The structures depicted below represent some non-limiting examples of types of optionally substituted phenyl. The names of the structures are indicted below the structures:

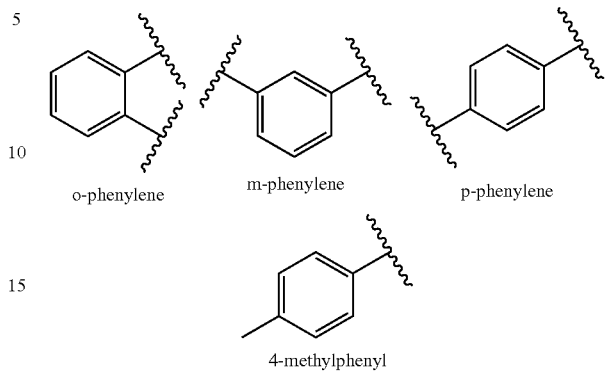

o-phenylene    m-phenylene    p-phenylene 4-methylphenyl

When optionally substituted, the addition of a substituent may occur at any possible position.

The names for several other moieties used herein are indicated with the corresponding structures below:

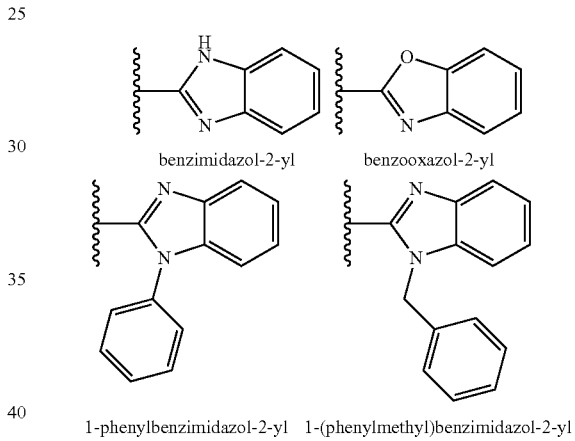

benzimidazol-2-yl    benzooxazol-2-yl 1-phenylbenzimidazol-2-yl    1-(phenylmethyl)benzimidazol-2-yl When optionally substituted, the addition of a substituent may occur at any possible position.

As used herein, the term "1-((4-halophenyl)methyl)benzimidazol-2-yl" refers to the ring system:

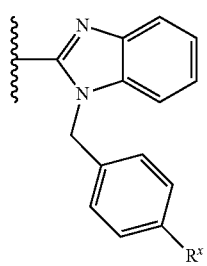

wherein $R^x$ may be a halogen such as F, Cl, Br, and I. When optionally substituted, the addition of a substituent may occur at any possible position.

An expression such as "$C_{1-10}$" (e.g. "$C_{1-10}$ alkyl") or "$C_{6-10}$" (e.g. "$C_{6-10}$ aryl") refers to the number of carbon atoms in a moiety, and similar expressions have similar meanings. If a moiety is optionally substituted, such as "optionally substituted "$C_{6-10}$ aryl," the designation of the number of carbon atoms such as "$C_{6-10}$" refers to the parent moiety only (e.g. the ring carbons of aryl) and does not characterize or limit any substituent on the moiety.

As used herein, the term "hydrocarbyl" refers to a moiety composed of carbon and hydrogen. Hydrocarbyl includes alkyl, alkenyl, alkynyl, aryl, etc., and combinations thereof, and may be linear, branched, cyclic, or a combination thereof. Hydrocarbyl may be bonded to any other number of moieties (e.g. be bonded to 1 other group, such as —$CH_3$, —$CH=CH_2$, etc.; 2 other groups, such as -phenyl-, —C≡C—, etc.; or any number of other groups) that the structure may bear, and in some embodiments, may contain from one to thirty-five carbon atoms. Examples of hydrocarbyl groups include but are not limited to $C_1$ alkyl, $C_2$ alkyl, $C_2$ alkenyl, $C_2$ alkynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.

As used herein the term "alkyl" refers to a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_6$ (e.g. cyclopropyl), $C_4H_8$ (e.g. cyclobutyl isomers such as cyclobutyl, methylcyclopropyl, etc.), $C_5H_{10}$ (e.g. cyclopentyl isomers such as cyclopentyl, methylcyclobutyl, dimethylcyclopropyl, etc.) $C_6H_{12}$ (e.g. cyclohexyl isomers), $C_7H_{15}$ (e.g. cycloheptyl isomers), etc.; and the like.

As used herein, the term "alkoxy" refers to —O-alkyl, such as —$OCH_3$, —$OC_2H_5$, —$OC_3H_7$ (e.g. propoxy isomers such as isopropoxy, n-propoxy, etc.), —$OC_4H_9$ (e.g. butyoxy isomers), —$OC_5H_{11}$ (e.g. pentoxy isomers), —$OC_6H_{13}$ (e.g. hexoxy isomers), —$OC_7H_{15}$ (e.g. heptoxy isomers), etc.

As used herein, the term "halo" refers to a halogen, such as F, Cl, Br, or I.

As used herein, the term "haloalkyl" refers to alkyl having one or more halo substituents. The term "fluoroalkyl" refers to alkyl having one or more fluoro substituents. The term "perfluoroalkyl" refers to fluoroalkyl wherein all hydrogen atom are replaced by fluoro such as —$CF_3$, —$C_2F_5$, —$C_3F_7$, —$C_4F_9$, etc.

As used herein, the term "acyl" refers to —$COR^0$, wherein $R^0$ may be optionally substituted hydrocarbyl. In some embodiments, acyl includes formyl, acetyl, propionoyl, butyryl, pentanoyl, hexanoyl, benzoyl, etc.

The term "work function" has the ordinary meaning known to one of ordinary skill in the art. In some embodiments, the "work function" of a metal refers to a measure of the minimum energy required to extract an electron from the surface of the metal.

The term "high work function metal" has the ordinary meaning known to one of ordinary skill in the art. In some embodiments, a "high work function metal" includes a metal or alloy that easily injects holes and typically has a work function greater than or equal to 4.5.

The term "low work function metal" has the ordinary meaning known to one of ordinary skill in the art. In some embodiments, a "low work function metal" includes a metal or alloy that easily loses electrons and typically has a work function less than 4.3.

Some embodiments provide a compound represented by Formula 1:

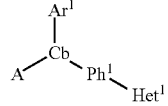

(Formula 1)

wherein Cb may be optionally substituted carbazole having a 3-position, a 6-position, and a 9-position. A attaches at the 3-position, and may be absent or may be $Ph^2$ or $Ph^2$-$Het^2$. In embodiments where A may be $Ph^2$ or $Ph^2$-$Het^2$, $Ph^2$ attaches directly to Cb at the 3-position. $Ph^1$ attaches to Cb at the 6-position, and $Ar^1$ attaches to Cb at the 9-position. In some embodiments, the optionally substituted carbazole has 0, 1, 2, 3, or 4 substituents independently selected from the group consisting of $C_{1-10}$ alkyl (such as $C_{1-10}$ linear alkyl, $C_{3-10}$ branched alkyl, or $C_{3-10}$ cycloalkyl), $C_{1-10}$ alkoxy, and halo.

With respect to Formula 1, A may be absent, or may be $Ph^2$ or $Ph^2$-$Het^2$. Thus, some embodiments relate to compounds represented by Formula 3, Formula 4, or Formula 5.

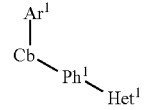

(Formula 3)

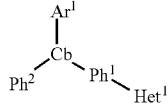

(Formula 4)

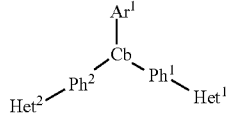

(Formula 5)

With respect to any relevant formula above, Cb may be optionally substituted carbazole. The optionally substituted carbazole may have 0, 1, 2, 3, or 4 substituents. In some embodiments, the substituents of Cb are not thiol, an ester, or an amide. In some embodiments, the substituents of Cb are independently selected from the group consisting of $C_{1-10}$ alkyl; hydroxyl; $C_{1-10}$ alkoxy; —$NR^1R^2$, wherein $R^1$ and $R^2$ are independently H or $C_{1-10}$ alkyl; halo; $C_{1-10}$ haloalkyl; $C_{1-10}$ perfluoroalkyl; $C_{1-10}$ acyl; $CO_2H$; cyano; cyanate; isocyanate; nitro; etc. In some embodiments, Cb has 0, 1, 2, 3, or 4 substituents independently selected from the group consisting of: $C_{1-10}$ alkyl, $C_{1-10}$ alkoxy, F, Cl, Br, and I. In some embodiments, Cb has 0, 1, 2, 3, or 4 substituents independently selected from the group consisting of: $C_{1-3}$ alkyl, F and Cl.

With respect to any relevant formula above, $Ar^1$ may be optionally substituted $C_{6-10}$ aryl. In some embodiments, $Ar^1$ may be phenyl or methylphenyl, each substituted with 0, 1, 2, 3, 4, or 5 substituents independently selected from: $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R'$, —$NR^1R^2$, —$C(O)NR^1R^2$, —$NR^1C(O)R^2$, —$OC(O)NR^1R^2$, or —$NR^1CO_2R^2$, wherein $R^1$ and $R^2$ are independently H or $C_{1-10}$ alkyl; cyano; cyanate; isocyanate; nitro; etc. In some embodiments, $Ar^1$ may be methylphenyl, such as 2-, 3-, or 4-methylphenyl, each optionally substituted with 1, 2, 3, or 4 substituents independently selected from $C_{1-3}$ alkyl, F and Cl.

With respect to any relevant formula above, $Ph^1$ may be optionally substituted phenyl. In some embodiments, $Ph^1$ may be phenyl, such as o-phenylene, m-phenylene, or p-phenylene, substituted with 0, 1, 2, 3, or 4 substituents independently selected from: $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$; —$NR^1R^2$, —$C(O)NR^1R^2$; —$NR^1C(O)R^2$; —$OC(O)NR^1R^2$; or —$NR^1CO_2R^2$, wherein $R^1$ and $R^2$ are independently H or $C_{1-10}$ alkyl; cyano; cyanate; isocyanate; nitro; etc. In some embodiments, $Ph^1$ may be phenyl, such as o-phenylene, m-phenylene, or p-phenylene, which has 0, 1, 2, 3, or 4 substituents independently selected from: $C_{1-10}$ alkyl; hydroxyl; halo; perfluoroalkyl; $C_{1-10}$ acyl; $C_{1-10}$ amides attaching at the carbonyl; $C_{1-10}$ esters attaching at the carbonyl; $CO_2H$; cyano; cyanate; isocyanate; nitro; etc. In some embodiments, $Ph^1$ may be phenyl, such as o-phenylene, m-phenylene, or p-phenylene, each optionally substituted with 1, 2, 3, or 4 substituents independently selected from the group consisting of: $C_{1-3}$ alkyl, F and Cl.

With respect to any relevant formula above, $Het^1$ may be optionally substituted benzimidazol-2-yl or optionally substituted benzooxazol-2-yl. In some embodiments, $Het^1$ may be selected from the group consisting of optionally substituted 1-phenylbenzimidazol-2-yl, optionally substituted 1-(phenylmethyl)benzimidazol-2-yl, and optionally substituted 1-((4-halophenyl)methyl)benzimidazol-2-yl. In some embodiments, $Het^1$ has 0, 1, 2, 3, 4, or 5 substituents independently selected from: optionally substituted $C_{6-30}$ aryl, $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$C(O)NR^1R^2$, —$NR^1C(O)R^2$, —$OC(O)NR^1R^2$, or —$NR^1CO_2R^2$, wherein $R^1$ and $R^2$ are independently H or $C_{1-10}$ alkyl; cyano; cyanate; isocyanate; nitro, etc.

In some embodiments, the substituents of $Het^1$ may include halo; $C_{1-10}$ perfluoroalkyl; $C_{1-10}$ acyl; optionally substituted $C_{6-30}$ aryl, $C_{1-10}$ alkyl, $C_{1-10}$ alkoxy, —$C(O)NR^1R^2$; —$CO_2R^1$; cyano; cyanate; isocyanate; nitro; etc. In some embodiments, $Het^1$ may be selected from the group consisting of 1-phenylbenzimidazol-2-yl, 1-(phenylmethyl)benzimidazol-2-yl, and 1-(4-halophenyl)methylbenzimidazol-2-yl, and $Het^1$ may be optionally substituted with 1, 2, 3, or 4 substituents independently selected from the group consisting of: optionally substituted $C_{6-30}$ aryl, $C_{1-10}$ alkyl, and $C_{1-10}$ alkoxy. In some embodiments, $Het^1$ may be benzooxazol-2-yl optionally substituted with 1, 2, 3, or 4 substituents independently selected from the group consisting of: optionally substituted $C_{6-30}$ aryl, $C_{1-10}$ alkyl, and $C_{1-10}$ alkoxy.

With respect to any relevant formula above, $Ph^2$ may be optionally substituted phenyl. In some embodiments, $Ph^2$ may be phenyl, such as o-phenylene, m-phenylene, or p-phenylene, which may be optionally substituted with 1, 2, 3, or 4, substituents independently selected from: $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$CONR^1R^2$, —$NR'COR^2$, —$OCONR^1R^2$, or —$NR^1CO_2R^2$, wherein $R^1$ and $R^2$ are independently H or $C_{1-10}$ alkyl; cyano; cyanate; isocyanate; nitro; etc. In some embodiments, $Ph^2$ may be phenyl, such as o-phenylene, m-phenylene, or p-phenylene, which is optionally substituted with 1, 2, 3, or 4 substituents independently selected from: $C_{1-10}$ alkyl; hydroxyl; halo; perfluoroalkyl; $C_{1-10}$ acyl; $C_{1-10}$ amides attaching at the carbonyl; $C_{1-10}$ esters attaching at the carbonyl; $CO_2H$; cyano; cyanate; isocyanate; nitro; etc. In some embodiments, $Ph^2$ may be unsubstituted. In some embodiments, $Ph^2$ may be phenyl, such as o-phenylene, m-phenylene, or p-phenylene, each optionally substituted with 1, 2, 3, or 4 substituents independently selected from the group consisting of: $C_{1-3}$ alkyl, F and Cl.

With respect to any relevant formula above, $Het^2$ may be optionally substituted benzimidazol-2-yl or optionally substituted benzooxazol-2-yl. In some embodiments, $Het^2$ may be selected from the group consisting of optionally substituted 1-phenylbenzimidazol-2-yl, optionally substituted 1-(phenylmethyl)benzimidazol-2-yl, and optionally substituted 1-((4-halophenyl)methyl)benzimidazol-2-yl. In some embodiments, $Het^2$ may have 0, 1, 2, 3, 4, or 5 substituents independently selected from: optionally substituted $C_{6-30}$ aryl, $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$CONR^1R^2$, —$NR^1COR^2$, —$OCONR^1R^2$, or —$NR^1CO_2R^2$, wherein $R^1$ and $R^2$ are independently H or $C_{1-10}$ alkyl; cyano; cyanate; isocyanate; nitro; etc. In some embodiments, the substituents of $Het^2$ may include halo; optionally substituted $C_{6-30}$ aryl; $C_{1-10}$ alkyl; $C_{1-10}$ alkoxy; perfluoroalkyl; $C_{1-10}$ acyl; $C_{0-10}$ amines such as $NR^1R^2$, wherein $R^1$ and $R^2$ are independently H or alkyl, such as $NH_2$, $NHCH_3$, $N(CH_3)_2$, etc.; $C_{1-10}$ amides attaching at the carbonyl; $C_{1-10}$ esters attaching at the carbonyl; —$CO_2CH_2$, etc.; $CO_2H$; cyano; cyanate; isocyanate; nitro; etc. In some embodiments, $Het^2$ may be selected from the group consisting of 1-phenylbenzimidazol-2-yl, 1-(phenylmethyl)benzimidazol-2-yl, and 1-((4-halophenyl)methyl)benzimidazol-2-yl, and $Het^2$ has 0, 1, 2, 3, or 4 substituents independently selected from the group consisting of: optionally substituted $C_{6-30}$ aryl, $C_{1-10}$ alkyl, or $C_{1-10}$ alkoxy.

With respect to Formula 2, in some embodiments, $R^a$, $R^b$, $R^c$, $R^d$, $R^e$, and $R^f$ may be independently selected from the group consisting of H, $C_{1-10}$ alkyl; hydroxyl; $C_{1-10}$ alkoxy; —$NR^1R^2$, wherein $R^1$ and $R^2$ are independently H or $C_{1-10}$ alkyl; halo; $C_{1-10}$ haloalkyl; $C_{1-10}$ perfluoroalkyl; $C_{1-10}$ acyl; $CO_2H$; cyano; cyanate; isocyanate; nitro; etc. In some embodiments, $R^a$, $R^b$, $R^c$, $R^d$, $R^e$, and $R^f$ may be independently selected from the group consisting of: H, $C_{1-10}$ alkyl, $C_{1-10}$ alkoxy, F, Cl, Br, and I. $R^a$, $R^b$, $R^c$, $R^d$, $R^e$, and d $R^f$ may be independently selected from the group consisting of: H, $C_{1-3}$ alkyl, F and Cl.

With respect to Formula 3, in some embodiments, $Ar^1$ may be optionally substituted phenyl, $Ph^1$ may be optionally substituted o-phenylene, and $Het^1$ may be optionally substituted 1-phenylbenzimidazol-2-yl. In some embodiments, the substituents of $Ar^1$, Cb, $Ph^1$, and $Het^1$ may be independently selected from: $C_{1-6}$ alkyl; hydroxyl; $C_{1-6}$ alkoxy; halo; $C_{1-6}$ perfluoroalkyl; $C_{1-6}$ acyl; —$CO_2R^5$, —$OC(O)R^5$, —$NR^5R^6$, —$C(O)NR^5R^6$, —$NR^5C(O)R^6$, —$OC(O)NR^5R^6$, or —$NR^5CO_2R^6$, wherein $R^5$ and $R^6$ are independently H or $C_{1-5}$ alkyl; cyano; cyanate; isocyanate; and nitro. In some embodiments, the substituents of $Ar^1$, Cb, $Ph^1$, and $Het^1$ may be independently selected from: $C_{1-3}$ alkyl, hydroxyl, $C_{1-3}$ alkoxy, F, Cl, Br, I, and $C_{1-3}$ perfluoroalkyl.

With respect to Formula 4, in some embodiments, $Ar^1$ may be optionally substituted phenyl, $Ph^1$ may be optionally substituted m-phenylene, and $Het^1$ may be optionally substituted 1-phenylbenzimidazol-2-yl. In some embodiments, $Ar^1$ may be optionally substituted phenyl, $Ph^1$ may be optionally substituted p-phenylene, and $Het^1$ may be optionally substituted 1-phenylbenzimidazol-2-yl. In some embodiments, $Ar^1$ may be optionally substituted phenyl, $Ph^1$ may be optionally substituted m-phenylene, and Het¹ may be optionally substituted benzooxazol-2-yl. In some embodiments, Ar¹ may be optionally substituted phenyl, Ph¹ may be optionally substituted o-phenylene, and Het¹ may be optionally substituted benzooxazol-2-yl. In some embodiments, Ar¹ may be optionally substituted phenyl, Ph¹ may be optionally substituted p-phenylene, and Het¹ may be optionally substituted benzooxazol-2-yl. In some embodiments, the substituents of Ar¹, Cb, Ph¹, Ph¹, and Het¹ may be independently selected from: $C_{1-6}$ alkyl; hydroxyl; $C_{1-6}$ alkoxy; halo; $C_{1-6}$ perfluoroalkyl; $C_{1-6}$ acyl; —$CO_2R^5$, —$OC(O)R^5$, —$NR^5R^6$, —$C(O)NR^5R^6$, —$NR^5C(O)R^6$, —$OC(O)NR^5R^6$, or —$NR^5CO_2R^6$, wherein $R^5$ and $R^6$ are independently H or $C_{1-5}$ alkyl; cyano; cyanate; isocyanate; and nitro. In some embodiments, the substituents of Ar¹, Cb, Ph¹, Ph², and Het¹ may be independently selected from: $C_{1-3}$ alkyl, hydroxyl, $C_{1-3}$ alkoxy, F, Cl, Br, I, and $C_{1-3}$ perfluoroalkyl.

With respect to Formula 5, in some embodiments Ar¹ may be optionally substituted phenyl, Ph¹ and Ph² are independently optionally substituted p-phenylene, and Het¹ and Het² are independently optionally substituted 1-phenylbenzimidazol-2-yl. In some embodiments Ar¹ may be optionally substituted phenyl, Ph¹ and Ph² are independently optionally substituted m-phenylene, and Het¹ and Het² are independently optionally substituted 1-phenylbenzimidazol-2-yl. In some embodiments Ar¹ may be optionally substituted phenyl, Ph¹ and Ph² are independently optionally substituted o-phenylene, and Het¹ and Het² are independently optionally substituted 1-phenylbenzimidazol-2-yl. In some embodiments Ar¹ may be optionally substituted phenyl, Ph¹ and Ph² are independently optionally substituted p-phenylene, and Het¹ and Het² are independently optionally substituted benzooxazol-2-yl. In some embodiments Ar¹ may be optionally substituted phenyl, Ph¹ and Ph² are independently optionally substituted m-phenylene, and Het¹ and Het² are independently optionally substituted benzooxazol-2-yl. In some embodiments Ar¹ may be optionally substituted phenyl, Ph¹ and Ph² are independently optionally substituted o-phenylene, and Het¹ and Het² are independently optionally substituted benzooxazol-2-yl. In some embodiments, the substituents of Ar¹, Cb, Ph¹, Ph², Het¹, and Het² may be independently selected from: $C_{1-6}$ alkyl; hydroxyl; $C_{1-6}$ alkoxy; halo; $C_{1-6}$ perfluoroalkyl; $C_{1-6}$ acyl; —$CO_2R^5$, —$OC(O)R^5$, —$NR^5R^6$, —$C(O)NR^5R^6$, —$NR^5C(O)R^6$, —$OC(O)NR^5R^6$, or —$NR^5CO_2R^6$, wherein $R^5$ and $R^6$ are independently H or $C_{1-5}$ alkyl; cyano; cyanate; isocyanate; and nitro. In some embodiments, the substituents of Ar¹, Cb, Ph¹, Ph², Het¹, and Het² may be independently selected from: $C_{1-3}$ alkyl, hydroxyl, $C_{1-3}$ alkoxy, F, Cl, Br, I, and $C_{1-3}$ perfluoroalkyl.

In some embodiments related to Formula 1 or Formula 2, A is the same as Ph¹-Het¹. Similarly, with respect to Formula 5, in some embodiments Ph¹-Het¹ is the same as Ph²-Het².

Some embodiments relate to compounds selected from:

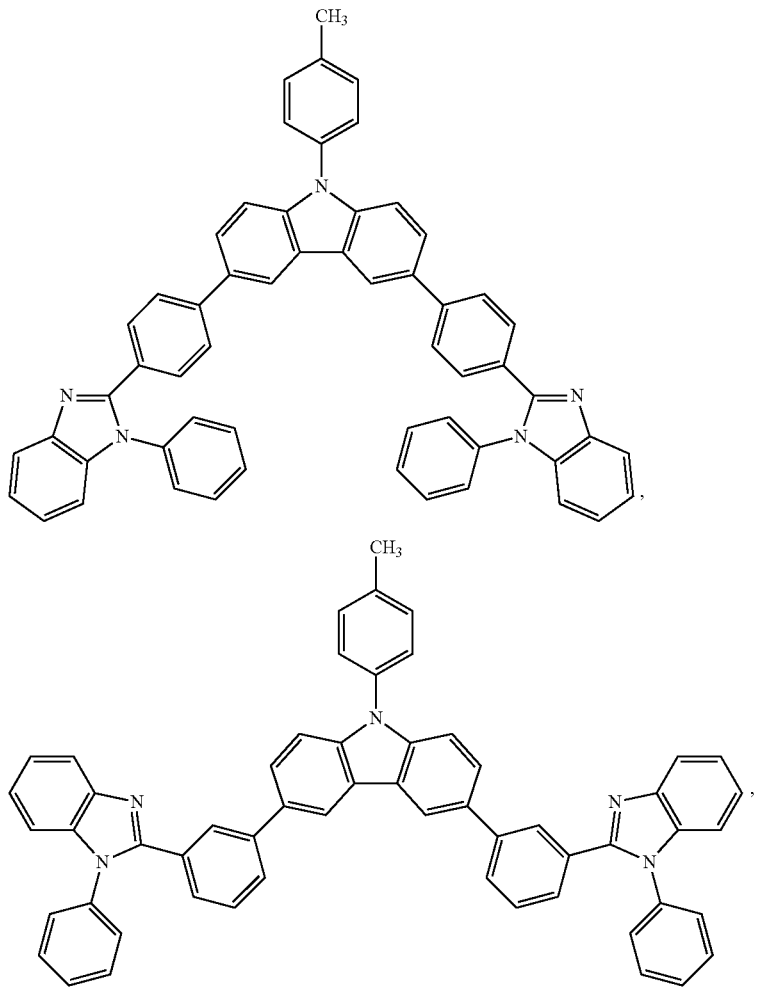

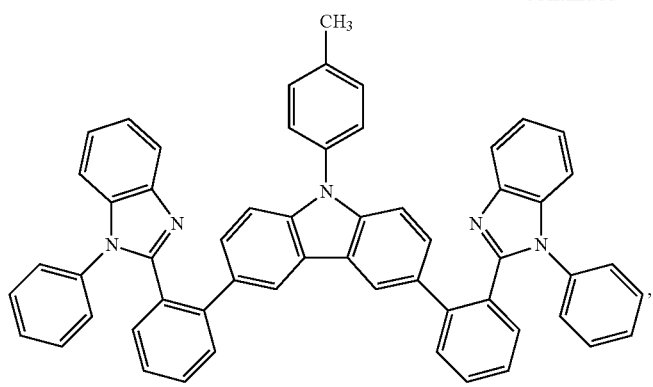
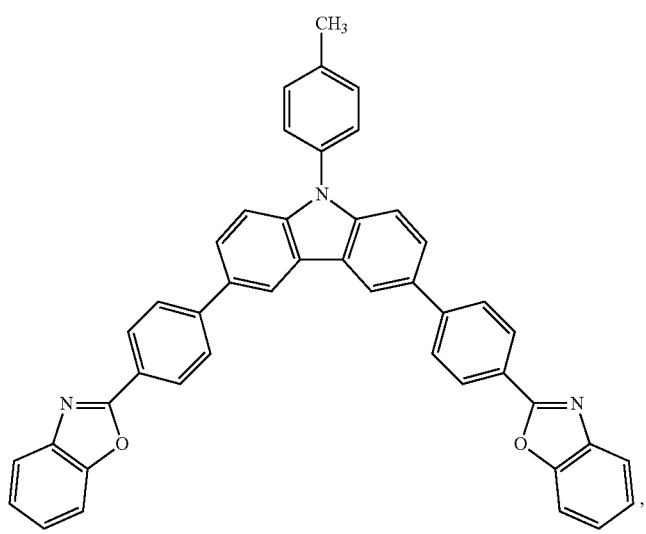
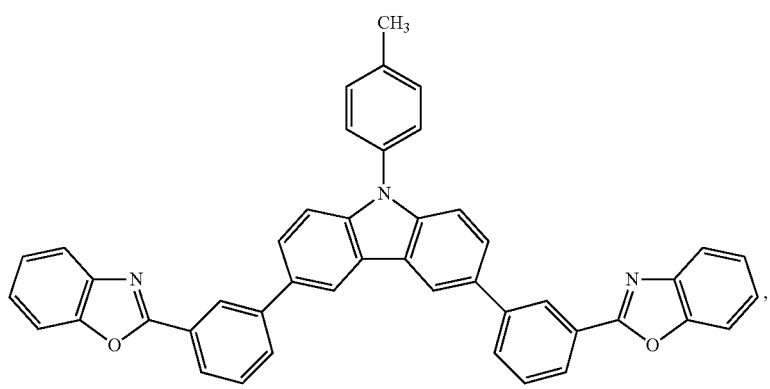
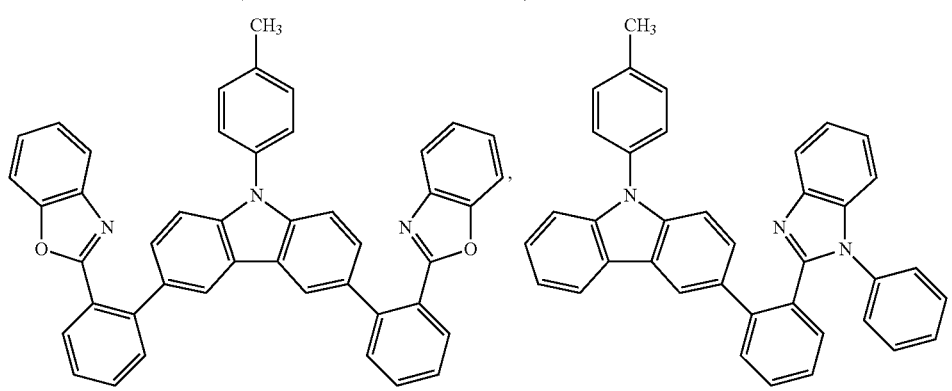

-continued

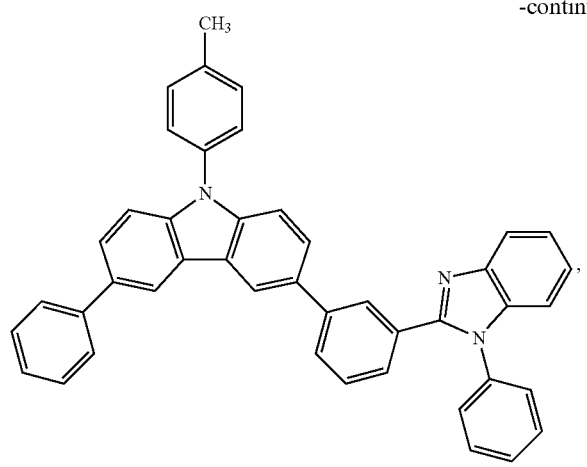

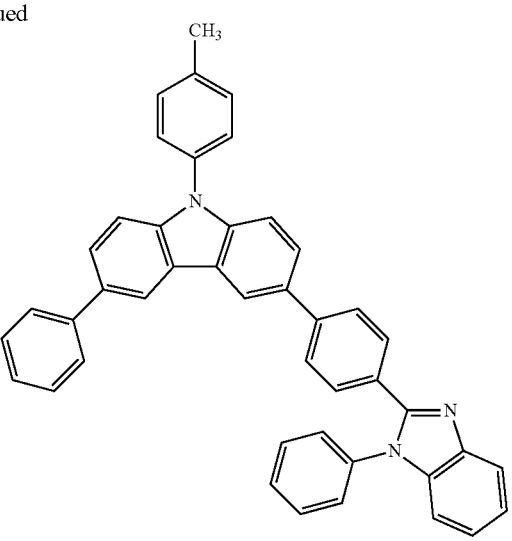

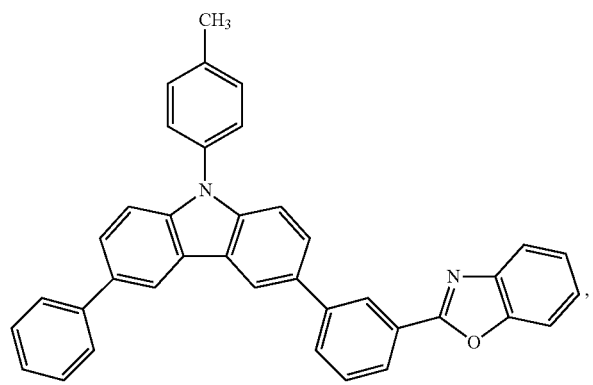

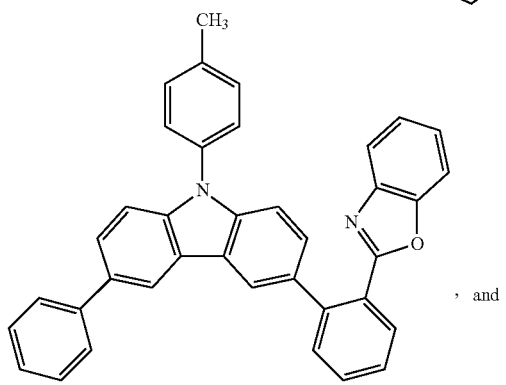

, and

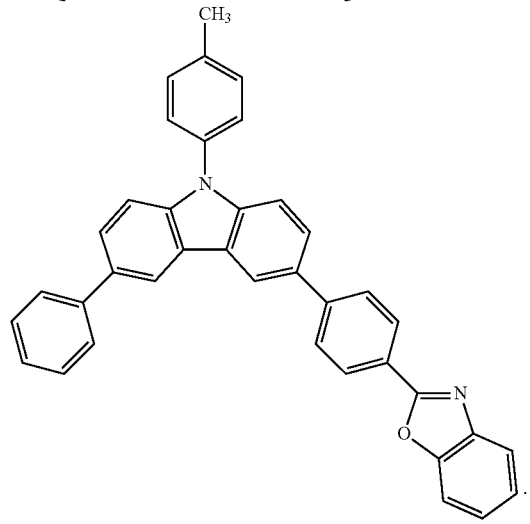

.

In some embodiments, the compounds described may be used as an emissive compound, as an ambipolar host in an organic light emitting diode emissive layer, or both. In some embodiments, the compounds disclosed herein may provide well balanced hole-transport and electron-transport mobility, which may lead to a simpler device structure with high quantum efficiency and low turn-on voltage. For example in some embodiments, the organic light emitting diode or device incorporating the presently described compounds may not have a hole transporting layer or an emissive layer. In some embodiments, these compounds may have high electro-chemical stability, high thermal stability, a high glass transition temperature (Tg), and high photostability. Thus, these compounds may provide an OLED device with a longer lifetime than existing OLED devices.

The compounds and compositions described herein can be incorporated into light-emitting devices in various ways. For example, an embodiment provides a light-emitting device comprising: an anode layer comprising a high work function metal; a cathode layer comprising a low work function metal; and a light-emitting layer positioned between the anode layer and the cathode layer. The light-emitting device may be configured so that the anode can transfer holes to the light-emitting layer and the cathode can transfer electrons to the light-emitting layer. The light-emitting layer comprises the compounds and/or compositions disclosed herein.

An anode layer may comprise a conventional material such as a metal, mixed metal, alloy, metal oxide or mixed-metal oxide, or a conductive polymer. Examples of suitable metals include the metals in Groups 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

The amount of the compounds disclosed herein in the light-emitting composition can vary. In one embodiment, the amount of a compound disclosed herein in the light-emitting layer may be in the range of from about 1% to about 100% by weight of the light-emitting layer. In another embodiment, the amount of a compound disclosed herein in the light-emitting layer may be in the range of from about 90% to about 99% by weight of the light-emitting layer. In another embodiment, the amount of a compound disclosed herein in the light-emitting layer may be about 97% by weight of the light-emitting layer. In some embodiments, the mass of the electroluminescent compound may be about 0.1% to about 10%, about 1% to about 5%, or about 3% of the mass of the emissive layer.

The thickness of the light-emitting layer may vary. In one embodiment, the light-emitting layer has a thickness in the range of from about 5 nm to about 200 nm. In another embodiment, the light-emitting layer has a thickness in the range of about 10 nm to about 150 nm.

In another embodiment, the light-emitting layer may also be configured to emit white light.

The compounds and compositions described herein may be useful in an emissive layer without requiring any additional hole-transport or electron-transport materials. Thus, in some embodiments, the light-emitting layer consists essentially of an electroluminescent compound and a compound disclosed herein. In some embodiments, the light-emitting layer consists essentially of a compound disclosed herein. In some embodiments, the light-emitting layer may comprise at least one hole-transport material or electron transport material in addition to a compound disclosed herein.

In some embodiments, a hole-transport material may comprise at least one of an aromatic-substituted amine, a carbazole, a polyvinylcarbazole (PVK), e.g. poly(9-vinylcarbazole); N,N'-bis(3-methylphenyl)N,N'-diphenyl-[1,1'-biphenyl]-4,4'-diamine (TPD); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-Tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (NPB); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); poly(9-vinylcarbazole) (PVK); a benzidine; a phenylenediamine; a phthalocyanine metal complex; a polyacetylene; a polythiophene; a triphenylamine; an oxadiazole; copper phthalocyanine; N,N'N"-1,3,5-tricarbazoloylbenzene (tCP); N,N'-bis(4-butylphenyl)-N,N'-bis(phenyl)benzidine; and the like.

In some embodiments, an electron-transport material may comprise at least one of 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer may be aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device comprises no electron transport or hole transport layer. In some embodiments, the device consists essentially of the anode layer, the cathode layer, and the light-emitting layer. In other embodiments, the light-emitting device may further comprise a hole-transport layer disposed between the anode and the light-emitting layer. The hole-transport layer may comprise at least one hole-transport material. Suitable hole-transport materials may include those listed above in addition to any others known to those skilled in the art.

In some embodiments, the light-emitting device may further comprise an electron-transport layer disposed between the cathode and the light-emitting layer. The electron-transport layer may comprise at least one electron-transport material. Suitable electron transport materials include those listed above and any others known to those skilled in the art.

If desired, additional layers may be included in the light-emitting device. These additional layers may include an electron injection layer (EIL), a hole blocking layer (HBL), an exciton blocking layer (EBL), and/or a hole injection layer (HIL). In addition to separate layers, some of these materials may be combined into a single layer.

In some embodiments, the light-emitting device can include an electron injection layer between the cathode layer and the light emitting layer. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tertbutylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer may be aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In an embodiment, the band gap of the material(s) that comprise an exciton blocking layer may be large enough to substantially prevent the diffusion of excitons. A number of suitable exciton blocking materials that can be included in an exciton blocking layer are known to those skilled in the art. Examples of material(s) that can compose an exciton blocking layer include an optionally substituted compound selected from the following: aluminum quinolate (Alq$_3$), 4,4'-bis[N-(naphthyl)-N-phenyl-amino]biphenyl (NPB), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) may include an optionally substituted compound selected from the following: a polythiophene derivative such as poly (3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino) phenyl-1,3,4-oxadiazol-2-yl)benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

The emissive compositions may be prepared by adapting methods known in the art for other emissive compositions. For example, the emissive compositions may be prepared by dissolving or dispersing the electroluminescent compound (including any compound described herein) and any host (including any compound described herein), if present, in a solvent and depositing the composition on the appropriate layer of the device. The liquid may be a single phase, or may comprise one or more additional solid or liquid phases dispersed in it. The solvent may then be allowed to evaporate, or the solvent may be removed via heat or vacuum, to provide an emissive composition. Alternatively, an electroluminescent compound may be melted, or added to a molten or liquid host material (if present). The molten composition may then be applied as a layer into the device, and allowed to solidify to provide a viscous liquid or solid emissive composition layer.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein, and an optional electroluminescent compound, can be deposited on the anode. The cathode layer, comprising a low work functioning metal (e.g., Mg:Ag), can then be deposited, e.g., vapor evaporated, onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

In some embodiments, the OLED may be configured by a wet process such as a process that comprises at least one of spraying, spin coating, drop casting, inkjet printing, screen printing, etc. Some embodiments provide a composition which may be a liquid suitable for deposition onto a substrate. The liquid may be a single phase, or may comprise one or more additional solid or liquid phases dispersed in it. The liquid typically comprises a light-emitting compound, a host material disclosed herein and a solvent.

Phototherapy

The devices disclosed herein may be useful in phototherapy. Typically, phototherapy involves exposing at least a portion of the tissue of a mammal with light, such as light from a device described herein.

The phototherapy may have a therapeutic effect, such as the diagnosis, cure, mitigation, treatment, or prevention of disease, or otherwise affecting the structure or function of the body of man or other animals. Some examples of conditions that phototherapy may be useful to treat or diagnose include, but are not limited to, infection, cancer/tumors, cardiovascular conditions, dermatological conditions, a condition affecting the eye, obesity, pain or inflammation, conditions related to immune response, etc.

Examples of infections may include microbial infection such as bacterial infection, viral infection, fungus infection, protozoa infection, etc.

Exemplary cancer or tumor tissues include vascular endothelial tissue, an abnormal vascular wall of a tumor, a solid tumor, a tumor of a head, a tumor of the brain, a tumor of a neck, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in a vascular system, a diseased bone marrow, diseased cells in which the disease may be one of an autoimmune and an inflammatory disease, etc.

Examples of cardiovascular conditions may include myocardial infarction, stroke, lesions in a vascular system, such as atherosclerotic lesions, arteriovenous malformations, aneurysms, venous lesions, etc. For example, a target vascular tissue may be destroyed by cutting off circulation to the desired location.

Examples of dermatological conditions may include hair loss, hair growth, acne, psoriasis, wrinkles, discoloration, skin cancer, rosacea, etc.

Examples of eye conditions may include age related macular degeneration (AMD), glaucoma, diabetic retinopathy, neovascular disease, pathological myopia, ocular histoplasmosis, etc.

Examples of pain or inflammation include arthritis, carpal tunnel, metatarsalgia, plantar fasciitis, TMJ, pain or inflammation affecting an elbow, an ankle, a hip, a hand, etc. Examples of conditions related to immune response may include, HIV or other autoimmune disease, organ transplant rejection, etc.

Other non-limiting uses of phototherapy may include treating benign prostate hyperplasia, treating conditions affecting adipose tissue, wound healing, inhibiting cell growth, and preserving donated blood.

The light itself may be at least partially responsible for the therapeutic effects of the phototherapy, thus phototherapy may be carried out without a photosensitive compound. In embodiments where a photosensitive compound is not used, light in the red range (approximately 630 nm to 700 nm) may decrease inflammation in injured tissue, increase ATP production, and otherwise stimulate beneficial cellular activity.

In some embodiments, where a photosensitive compound is not used, light in the red range (approximately 600 nm to 700 nm) can be used in combination with wound dressings to effect accelerated wound healing. The wound dressing may include a hydrocolloid particles or material, for example as described in US 2008031178 (Ishikura, Jun, et al, filed Jun. 4, 2008); a transparent film, for example as described in U.S. Pat. No. 7,678,959 issued Mar. 16, 2010 to Okadam Katshiro, et al.; and/or an adhesive material. An adhesive may be any conventional adhesive and may have sufficient strength to keep the wound dressing or device in contact with a patient while not having too much strength such that wound dressing cannot be removed from the patient.

In some embodiments, at least a portion of a wound dressing is exposed to light from a device. The wound dressing may be applied to the wound of a mammal to effect accelerated healing. The dressing may be exposed to the light prior to and/or subsequent to application of the dressing to the wound site. Light in the red range may also be used in conjunction with light of other spectral wavelengths, for example blue or yellow, to facilitate post operative healing. Facial rejuvenation may be effected by applying about 633 nm radiation to the desired tissue for about 20 minutes. In some embodiments, facial skin rejuvenation is believed to be attained by applying light in the red range for a therapeutically effective amount of time.

The light may also be used in conjunction with a photosensitive compound. The photosensitive compound may be administered directly or indirectly to body tissue so that the photosensitive compound is in or on the tissue. At least a portion of the photosensitive compound may then be activated by exposing at least a portion of tissue with light.

For example, a photosensitive compound may be administered systemically by ingestion or injection, topically applying the compound to a specific treatment site on a patient's body, or by some other method. This may be followed by illumination of the treatment site with light having a wavelength or waveband corresponding to a characteristic absorption waveband of the photosensitive compound, such as about 500 or about 600 nm to about 800 nm or about 1100 nm, which activates the photosensitive compound. Activating the photosensitive compound may cause singlet oxygen radicals and other reactive species to be generated, which may lead to a number of biological effects that may destroy the tissue which has absorbed the photosensitive compound such as abnormal or diseased tissue.

The photosensitive compound may be any compound, or pharmaceutically acceptable salts or hydrates thereof, which may react as a direct or indirect result of absorption of ultraviolet, visible, or infrared light. In some embodiment, the photosensitive compound may react as a direct or indirect result of absorption of visible light, such as red light, orange light, yellow light, green light, blue light, indigo light, violet light, or a combination thereof. In some circumstances, a photosensitive compound which may react as a direct or indirect result of absorption of red light may be useful to provide deeper penetration of visible light into tissue. The photosensitive compound may be a compound which is not naturally in the tissue. Alternatively, the photosensitive compound may naturally be present in the tissue, but an additional amount of the photosensitive compound may be administered to the mammal. In some embodiments, the photosensitive compound may selectively bind to one or more types of selected target cells and, when exposed to light of an appropriate waveband, may absorb the light, which may cause substances to be produced that impair or destroy the target cells.

While not limiting any embodiment, for some types of therapies, it may be helpful if the photosensitive compound or the photodegradation products of the photosensitive compound are sufficiently nontoxic. For example, a therapeutic index (i.e. the LD50/ED50 ratio, or the ratio of the lethal dose for 50% of the population to the effective dose for 50% of the population) of at least 2, at least 5, at least 10, at least 100, or at least 1000, may be desirable for the photosensitive compound or photodegradtion products of the photosensitive compound.

Some non-limiting examples of photosensitive chemicals may be found in Kreimer-Bimbaum, Sem. Hematol, 26:157-73, (1989), incorporated by reference herein in its entirety, and may include, but are not limited to, chlorins, e.g., Tetrahydroxylphenyl chlorin (THPC) [652 nm], bacteriochlorins [765 nm], e.g., N-Aspartyl chlorin e6 [664 nm], phthalocyanines [600-700 nm], porphyrins, e.g., hematoporphyrin [HPD][630 nm], purpurins, e.g., [1,2,4-Trihydroxyanthraquinone] Tin Etiopurpurin [660 nm], merocyanines, psoralens, benzoporphyrin derivatives (BPD), e.g., verteporfin, and porfimer sodium; and pro-drugs such as delta-aminolevulinic acid or methyl aminolevulinate, which can produce photosensitive agents such as protoporphyrin IX. Other suitable photosensitive compounds may include indocyanine green (ICG) [800 nm], methylene blue [668 nm, 609 nm], toluidine blue, texaphyrins, Talaportin Sodium (mono-L-aspartyl chlorine)[664 nm], verteprofin [693 nm], which may be useful for phototherapy treatment of conditions such as age-related macular degeneration, ocular histoplasmosis, or pathologic myopia], lutetium texaphyrin [732 nm], and rostaporfin [664 nm].

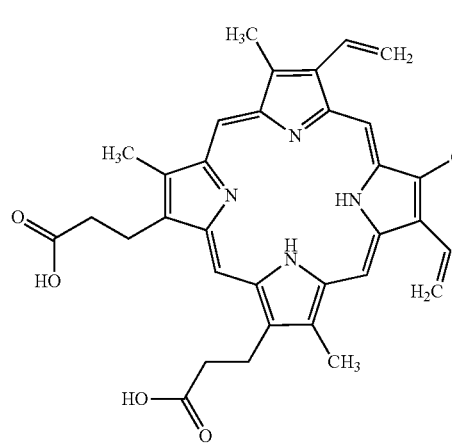

protoporphyrin IX

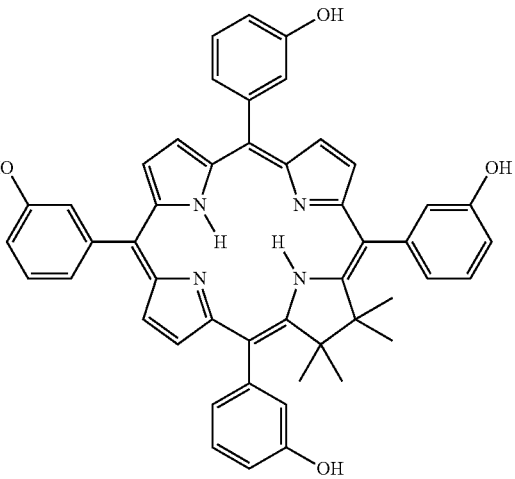

Tetrahydroxylphenyl chlorin (THPC)

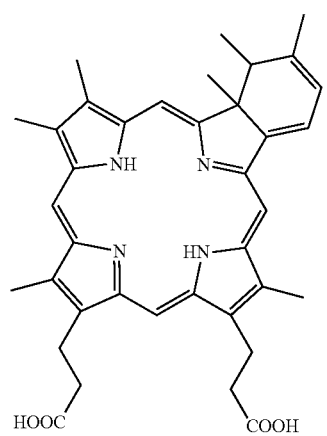

benzoporphyrin
732 nm

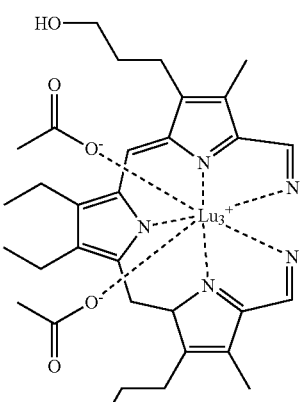

Motexafin lutetium

In some embodiments, the photosensitive compound comprises at least one component of porfimer sodium. Porfimer sodium comprises a mixture of oligomers formed by ether and ester linkages of up to eight porphorin units. The structural formula below is representative of some of the compounds present in porfimer sodium, wherein n may be 0, 1, 2, 3, 4, 5, or 6 and each R may be independently —CH(OH)CH$_3$ or —CH=CH$_2$.

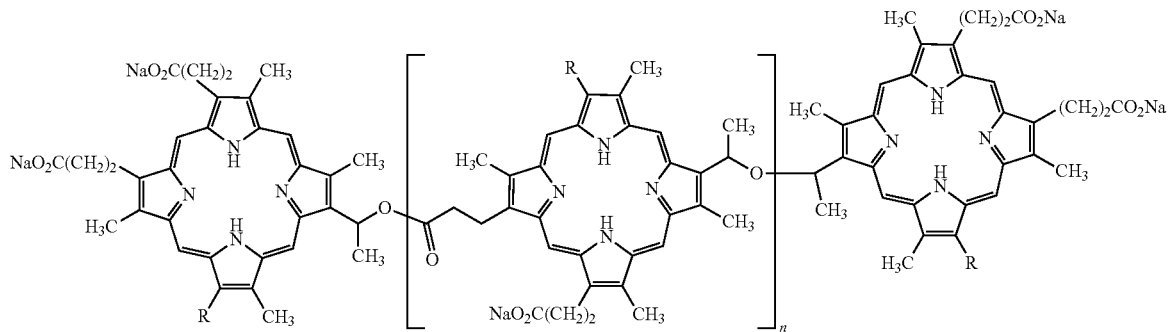

In some embodiments, the photosensitive compound may be at least one of the regioisomers of verteporphin, shown below.

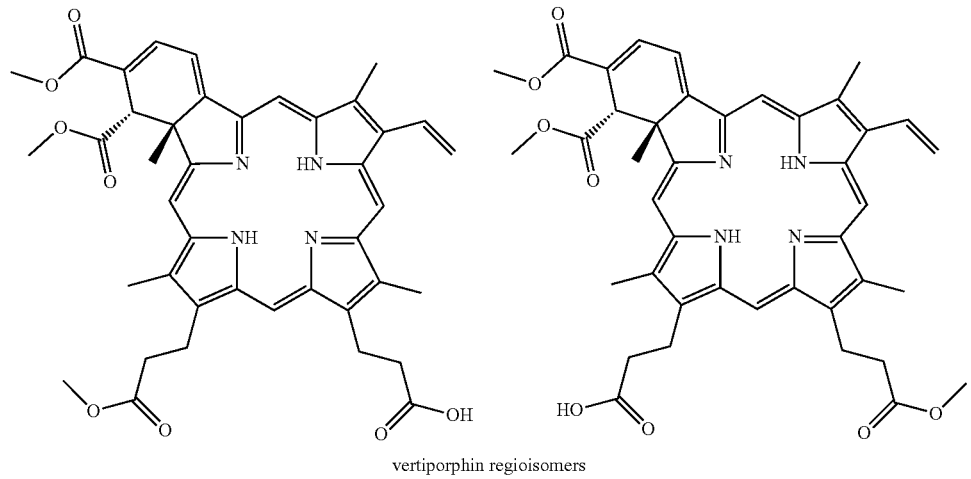

vertiporphin regioisomers

In some embodiments, the photosensitive compound may comprise a metal analogue of phthalocyanine shown below.

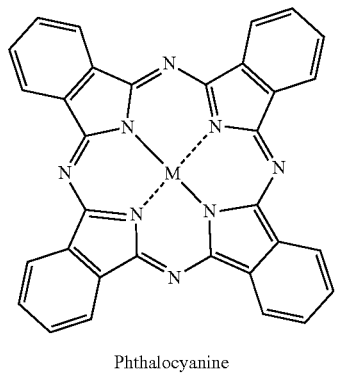

Phthalocyanine

In one embodiment, M may be zinc. In one embodiment, the compound can be zinc phthalocyanine or zinc phthalocyanine tetrasulfonate.

A photosensitive agent can be administered in a dry formulation, such as a pill, a capsule, a suppository or a patch. The photosensitive agent may also be administered in a liquid formulation, either alone, with water, or with pharmaceutically acceptable excipients, such as those disclosed in Remington's Pharmaceutical Sciences. The liquid formulation also can be a suspension or an emulsion. Liposomal or lipophilic formulations may be desirable. If suspensions or emulsions are utilized, suitable excipients may include water, saline, dextrose, glycerol, and the like. These compositions may contain minor amounts of nontoxic auxiliary substances such as wetting or emulsifying agents, antioxidants, pH buffering agents, and the like. The above described formulations may be administered by methods which may include but are not limited to intradermal, intramuscular, intraperitoneal, intravenous, subcutaneous, intranasal, epidural, oral, sublingual, intranasal, intracerebral, intravaginal, transdermal, iontophoretical, rectally, by inhalation, or topically to the desired target area, for example, the body cavity (oral, nasal, rectal), ears, nose, eyes, or skin. The preferred mode of administration may be left to the discretion of the practitioner, and may depend in part upon the site of the medical condition (such as the site of cancer or viral infection).

The dose of photosensitive agent may vary. For example, the target tissue, cells, or composition, the optimal blood level, the animal's weight, and the timing and duration of the radiation administered, may affect the amount of photosensitive agent used. Depending on the photosensitive agent used, an equivalent optimal therapeutic level may have to be empirically established. The dose may be calculated to obtain a desired blood level of the photosensitive agent, which in some embodiments may be from about 0.001 g/mL or 0.01 µg/ml to about 100 µg/ml or about 1000 µg/ml.

In some embodiments, about 0.05 mg/kg or about 1 mg/kg to about 50 mg/kg or about 100 mg/kg may be administered to the mammal. Alternatively, for topical application, about 0.15 mg/m$^2$ or about 5 mg/m$^2$ to about 30 mg/m$^2$ or about 50 mg/m$^2$ may be administered to the surface of the tissue.

The light may be administered by an external or an internal light source, such as an OLED device described herein. The intensity of radiation or light used to treat the target cell or target tissue may vary. In some embodiments, the intensity may be about 0.1 mW/cm$^2$ to about 100 mW/cm$^2$, about 1 mW/cm$^2$ to about 50 mW/cm$^2$, or about 3 mW/cm$^2$ to about 30 mW/cm$^2$. The duration of radiation or light exposure administered to a subject may vary. In some embodiments the exposure ranges from about 1 minute, about 60 minutes, or about 2 hours to about 24 hours, about 48 hours, or about 72 hours.

A certain amount of light energy may be required to provide a therapeutic effect. For example, a certain amount of light energy may be required to activate the photosensitive compounds. This may be accomplished by using a higher power light source, which may provide the needed energy in a shorter period of time, or a lower power light source may be used for a longer period of time. Thus, a longer exposure to the light may allow a lower power light source to be used, while a higher power light source may allow the treatment to be done in a shorter time. In some embodiments, the total fluence or light energy administered during a treatment may be in the range of 5 Joules to 1,000 Joules, 20 Joules to 750 Joules, or 50 Joules to 500 Joules.

Figure 1:
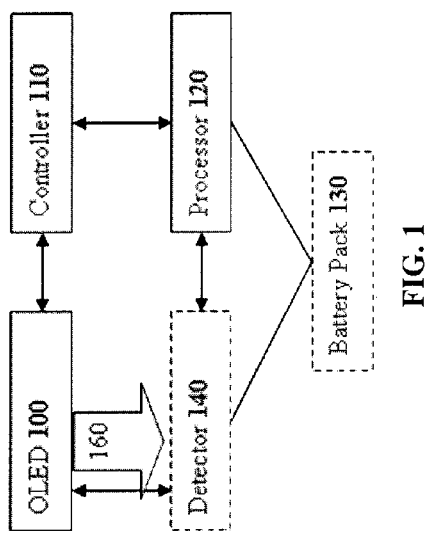
FIG. 1 is a schematic of an embodiment of a light-emitting device suitable for phototherapy which comprises a controller and a processor.

FIG. 1 is a schematic of some embodiments which further include a controller 110 and processor 120 electrically connected to an organic light-emitting diode 100 (OLED), which may help to provide a uniform power supply to facilitate homogeneous light exposure of the tissue. In some embodiments, the apparatus may further include an optional detector 140, such as photodiode, which may detect a portion of the light 160 emitted from the OLED 100, to help determine the amount of light being emitted by the OLED 100. For example, the detector 140 may communicate a signal related to the intensity of the light 160 received from the OLED 100 to the processor 120, which, based upon the signal received, may communicate any desired power output information to the controller 100. Thus, these embodiments may provide real time feedback which allows the control of the intensity of light emitted from the OLED 100. The detector 140 and the processor 120 may be powered by compact power supply, such as a battery pack 130, or by some other power source.

In some embodiments related to phototherapy, the LED device may further comprise a dosage component. A dosage component may be configured to provide a sufficient amount of light to activate a sufficient portion of a photosensitive compound to provide a therapeutic effect for treating a disease. For example, a dosage component may be a timer that is configured to deliver light from the device for an amount of time sufficient to deliver the appropriate light dosage. The timer may automatically stop the emission from the device once the appropriate light dosage has been delivered. The dosage component may also comprise a positioning component that positions the device so that emitted light is delivered to the appropriate area of a mammal body and is at an appropriate distance from the affected tissue to deliver an effective amount of light. The dosage component may be configured to work with a particular photosensitive compound, or may provide flexibility. For example, a physician, a veterinarian, or another appropriate medical practitioner may set the parameters of the dosage component for use by a patient outside of the practitioner's office, such as at the patient's home. In some embodiments, the device may be provided with a set of parameters for various photosensitive compounds to assist a medical practitioner in configuring the device.

In some embodiments, the device may further include a wireless transmitter electrically connected to an component of the apparatus generating treatment information, e.g., level of intensity, time of application, dosage amount, to communicate/transfer data to another external receiving device, such as cell phone, PDA or to doctor's office. In some embodiments, the apparatus may further include an adhesive tape which may be used to attach the apparatus on the tissue surface so as to stabilize it on the target area.

For phototherapy and other applications, a wavelength convertor may be positioned in the device to receive at least a portion of light emitted from the organic light-emitting diode in a lower wavelength range, such as about 350 nm to less than about 600 nm, and convert at least a portion of the light received to light in a higher wavelength range, such as about 600 nm to about 800 nm. The wavelength convertor may be a powder, a film, a plate, or in some other form and, may comprise: yttrium aluminum garnet (YAG), alumina ($Al_2O_3$), yttria ($Y_2O_3$), titania ($TiO_2$), and the like. In some embodiments, the wavelength convertor may comprise at least one dopant which is an atom or an ion of an element such as Cr, Ce, Gd, La, Tb, Pr, Sm, Eu, etc.

In some embodiments, translucent ceramic phosphor may be represented by a formula such as, but not limited to $(A_{1-x}E_x)_3D_5O_{12}$, $(Y_{1-x}E_x)_3D_5O_{12}$; $(Gd_{1-x}E_x)_3D_5O_{12}$; $(La_{1-x}E_x)_3D_5O_{12}$; $(Lu_{1-x}E_x)_3D_5O_{12}$; $(Tb_{1-x}E_x)_3D_5O_{12}$; $(A_{1-x}E_x)_3Al_5O_{12}$; $(A_{1-x}E_x)_3Ga_5O_{12}$; $(A_{1-x}E_x)_3In5O_{12}$; $(A_{1-x}Ce_x)_3D_5O_{12}$; $(A_{1-x}E_x)_3D_5O_{12}$; $(A_{1-x}Tb_x)_3D_5O_{12}$; $(A_{1-x}E_x)_3Nd_5O_{12}$; and the like. In some embodiments, the ceramic may comprise a garnet, such as a yttrium aluminum garnet, with a dopant. Some embodiments provide a composition represented by the formula $(Y_{1-x}Ce_x)_3Al_5O_{12}$. In any of the above formulas, A may be Y, Gd, La, Lu, Tb, or a combination thereof; D may be Al, Ga, In, or a combination thereof; E may be Ce, Eu, Tb, Nd, or a combination thereof; and x may be in the range of about 0.0001 to about 0.1, from about 0.0001 to about 0.05, or alternatively, from about 0.01 to about 0.03

Some embodiments include use of a device described herein for carrying out phototherapy.

In some embodiments, the phototherapy comprises exposing at least a portion of a tissue of a mammal to light from the device.

In some embodiments, the tissue comprises a photosensitive compound which is not naturally in the tissue, and wherein at least a portion of the photosensitive compound is activated by exposing the portion of the tissue to light from the device.

Some embodiments include use of a device described herein for treating a disease.

In some embodiments, treating the disease comprises administering a photosensitive compound to a tissue of a mammal in need thereof; exposing at least a portion of the tissue to light from the device; and wherein at least a portion of the photosensitive compound is activated by at least a portion of the light from the device to which the tissue is exposed, to thereby treat the disease.

In some embodiments, activating the photosensitive compound produces singlet oxygen.

In some embodiments, the photosensitive compound is 5-aminolevulinic acid, verteporfin, zinc phthalocyanine, or pharmaceutically acceptable salts thereof.

In some embodiments, the disease is cancer.
In some embodiments, the disease is a microbial infection.
In some embodiments, the disease is a skin condition.
In some embodiments, the disease is an eye condition.

Synthetic Examples

Example 1

Synthesis of Host-1

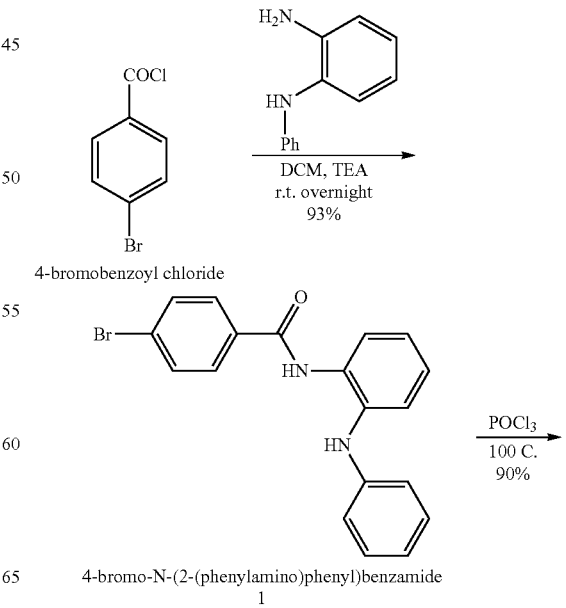

4-bromobenzoyl chloride 4-bromo-N-(2-(phenylamino)phenyl)benzamide
1

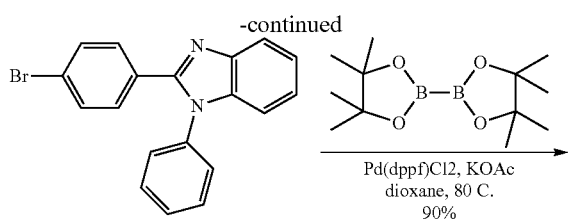

2-(4-bromophenyl)-1-phenyl-1H-benzo[d]imidazole
2

Pd(dppf)Cl2, KOAc
dioxane, 80 C.
90%

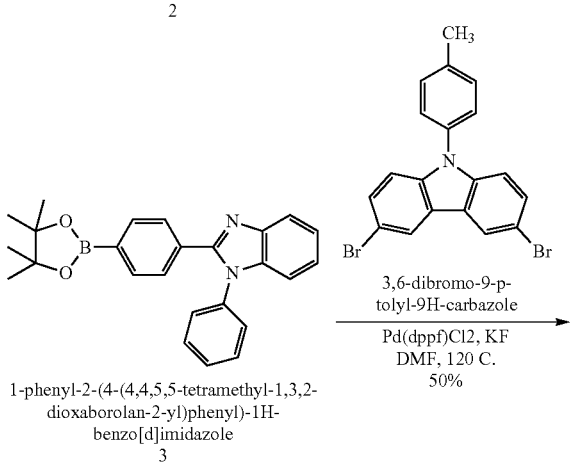

1-phenyl-2-(4-(4,4,5,5-tetramethyl-1,3,2-dioxaborolan-2-yl)phenyl)-1H-benzo[d]imidazole
3

3,6-dibromo-9-p-tolyl-9H-carbazole

Pd(dppf)Cl2, KF
DMF, 120 C.
50%

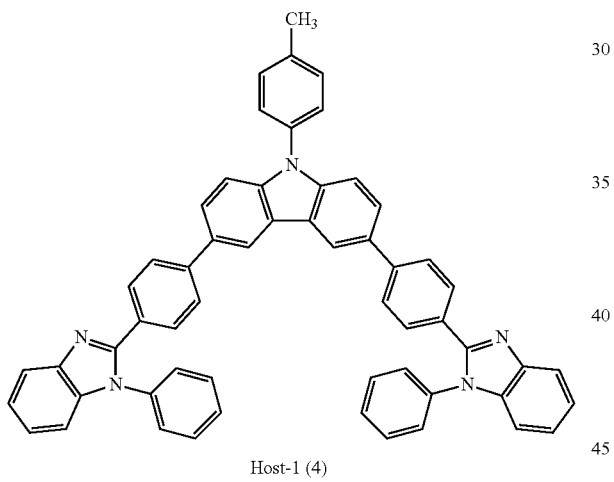

Host-1 (4)

4-Bromo-N-(2-(phenylamino)phenyl)benzamide (1)

To a solution of 4-bromo-benzoyl chloride (11 g, 50 mmol) in anhydrous dichloromethane (100 ml), was added N-phenylbenzene-1,2-diamine (10.2 g, 55 mmol), then triethylamine (17 ml, 122 mmol) slowly. The whole was stirred at room temperature overnight. Filtration gave a white solid (6.5 g). The filtrate was worked up with water (~300 ml) and extracted with dichloromethane (DCM) (~300 ml) three times. The organic phase was collected and dried over $MgSO_4$, concentrated and recrystallized in DCM/hexanes to give another portion of white solid (10.6 g). Total amount of product was 17.1 g, in 93% yield.

2-(4-bromophenyl)-1-phenyl-1H-benzo[d]imidazole (2)

To a suspension of amide (1) (9.6 g, 26 mmol) in anhydrous 1,4-dioxane (100 mL) was added $POCl_3$ (9.2 mL, 100 mmol) slowly. The whole was then heated at about 100° C. overnight. After cooling to room temperature, the mixture was poured into ice (200 g) with stirring. Filtration, followed by recrystallization in DCM/hexanes gave a pale grey solid (8.2 g, in 90% yield).

1-phenyl-2-(4-(4,4,5,5-tetramethyl-1,3,2-dioxaborolan-2-yl)phenyl)-1H-benzo[d]imidazole (3)

A mixture of compound (2) (0.70 g, 2 mmol), bis(pinacolate)diborane (0.533 g, 2.1 mmol), $Pd(dppf)Cl_2$ (0.060 g, 0.08 mmol) and anhydrous potassium acetate (0.393 g, 4 mmol) in 1,4-dioxane (20 mL) was heated at about 80° C. under argon overnight. After cooling to room temperature, the whole was diluted with ethyl acetate (~80 mL) then filtered. The solution was absorbed on silica gel, then purified by column chromatography (hexanes/ethyl acetate 5:1 to 3:1) to give a white solid (0.64 g, in 81% yield).

Host-1 (4)

A mixture of compound (3) (2.40 g, 6.06 mmol), 3,6-dibromo-9-p-tolyl-9H-carbazole (1.245 g, 3.0 mmol), $Pd(dppf)Cl_2$ (0.23 g, 0.31 mmol) and KF (1.05 g, 18.2 mmol) in anhydrous DMF (~50 mL) was heated at about 120° C. under argon overnight. After the mixture was cooled to room temperature, it was poured into water (~200 mL) and filtered. The solid was collected and dissolved in DCM (~200 mL). After removal of water by separate funnel followed by dried over $MgSO_4$, the DCM solution was absorbed on silica gel, purified by column chromatography (hexanes/ethyl acetate 4:1 to 2:1) and precipitated from ethyl acetate/hexanes to give an off-white solid (850 mg, in 36% yield).

Example 2

Synthesis of Host-2, Host-3

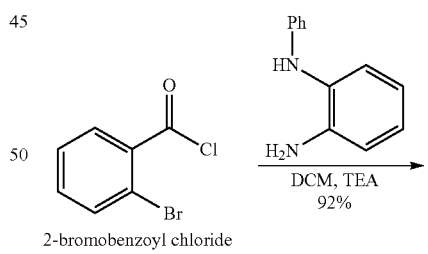

2-bromobenzoyl chloride

DCM, TEA
92%

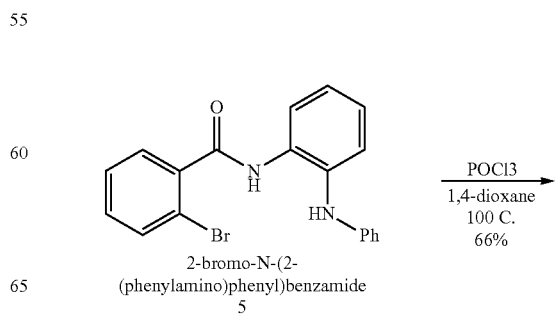

2-bromo-N-(2-(phenylamino)phenyl)benzamide
5

POCl3
1,4-dioxane
100 C.
66%

-continued

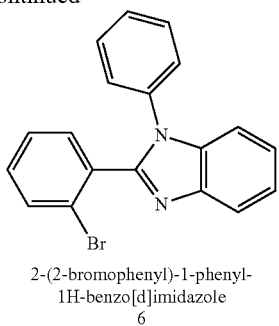

2-(2-bromophenyl)-1-phenyl-
1H-benzo[d]imidazole
6

9-p-tolyl-9H-carbazole-3,6-diyldiboronic acid

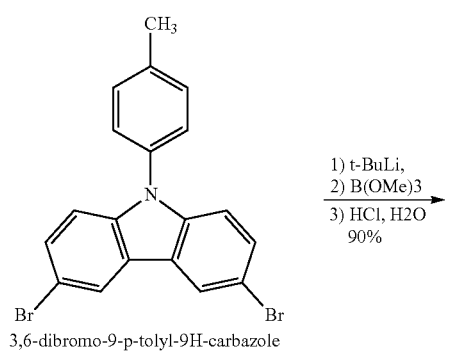

3,6-dibromo-9-p-tolyl-9H-carbazole 1) t-BuLi,
2) B(OMe)3
3) HCl, H2O
90%

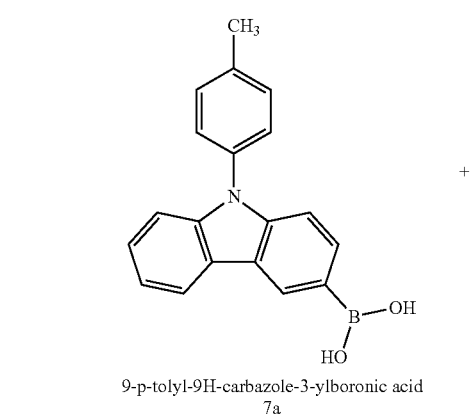

9-p-tolyl-9H-carbazole-3-ylboronic acid
7a

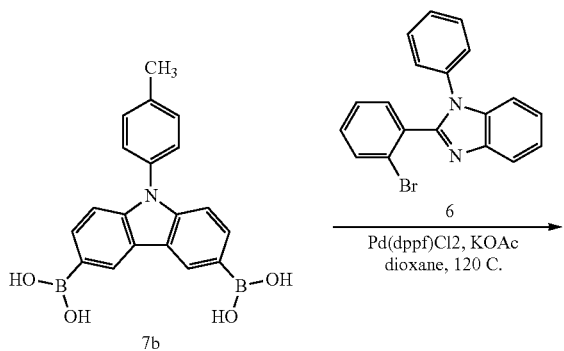

7b

Pd(dppf)Cl2, KOAc
dioxane, 120 C.

-continued

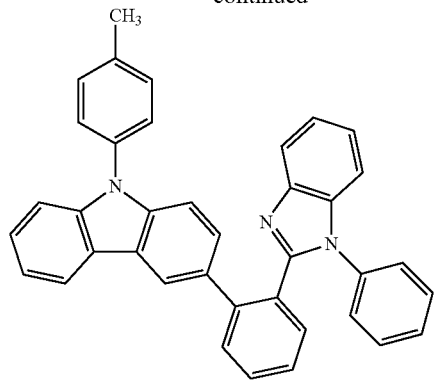

26%
Host-2
(8)

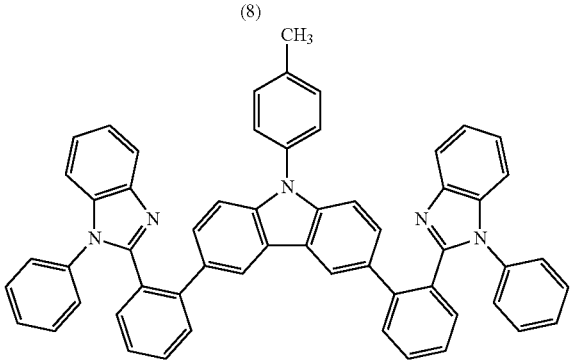

46%
Host-3
(9)

2-bromo-N-(2-(phenylamino)phenyl)benzamide (5)

To a solution of N-phenylbenzene-1,2-diamine (6.08 g, 30 mmol) in anhydrous dichloromethane (~100 mL), was added 2-bromobenzoylchloride (6.585 g, 33 mmol), followed by triethylamine (7.0 mL, 50 mmol) slowly with water bath cooling. After the additions, the whole was stirred at room temperature overnight. The resulting mixture was poured into water (~150 mL) and extracted with dichloromethane (~100 mL) twice. The organic phase was collected, dried over $Na_2SO_4$, concentrated and recrystallized in dichloromethane/hexanes to give a white solid (10.7 g, in 92% yield).

2-(2-bromophenyl)-1-phenyl-1H-benzo[d]imidazole
(6)

To a solution of 2-bromo-N-(2-(phenylamino)phenyl)benzamide (10.7 g, 29 mmol) in anhydrous 1,4-dioxane (~100 mL), was added $POCl_3$ (6.92 g, 45 mmol) slowly. The whole was heated to about 100° C. under argon overnight. After cooling the mixture to room temperature, the mixture was poured into ice (~150 g), and then neutralized with $NaHCO_3$. After filtration, the solid was collected then dissolved in dichloromethane (~250 mL), which was washed with water (~250 mL). The aqueous solution was extracted with dichloromethane (~100 mL×2). The organic phase was combined and dried over $Na_2SO_4$, concentrated, and recrystallized in dichloromethane/hexanes to give a light grey solid (6.68 g, 66% yield).

9-p-Tolyl-9H-carbazole-3,6-diyldiboronic acid and 9-p-tolyl-9H-carbazol-3-ylboronic acid (7)

To a solution of 3,6-dibromo-9-p-tolyl-9H-carbazole (4.15 g, 10 mmol) in anhydrous THF (100 mL) was added a solution of t-BuLi (1.7 M in pentane, 25 mL, 42 mmol) at about −78° C. slowly under argon. The whole was stirred for about 40 min at about −78° C., then to the resulting solution, a freshly distilled trimethyl borate (2.5 mL, 22 mmol) was added at about −78° C. After addition, the cooling bath was removed and the whole was allowed to stir at room temperature overnight.

To the resulting mixture, 5% HCl aqueous solution (~150 mL) was added and stirred overnight. The aqueous phase was separated and extracted with ethyl acetate (~150 mL×2). The organic phase was combined and dried over $Na_2SO_4$. After removal of solvent, a white solid was obtained (3.0 g), which was used for the next step without further purification. LCMS indicate the solid is a mixture of 9-p-tolyl-9H-carbazole-3,6-diyldiboronic acid and 9-p-tolyl-9H-carbazol-3-ylboronic acid (about 9:1 ratio from peak intensity).

Host-2 (8) and Host-3 (9)

A mixture of 7 (1.66 g), benzimidazole 6 (1.5 g, 4.3 mmol), $Pd(dppf)Cl_2$ (200 mg, 0.27 mmol) and KF (1.4 g, 24 mmol) in DMF (40 mL) was heated at about 125° C. under argon overnight. After cooling to room temperature, the mixture was poured into water (~150 mL). The precipitate was filtered, collected, and then redissolved in dichloromethane (~100 mL). After removal of water, the dichloromethane solution was dried over $Na_2SO_4$, absorbed on silica gel, and purified by column chromatography (hexanes/ethyl acetate, gradient 5:1 to 2:1). The first blue fluorescent fraction was concentrated and recrystallized in dichloromethane/hexanes to give Host-2 (8) 600 mg, in 26% yield. The second blue fluorescent fraction was concentrated and recrystallized in dichloromethane/hexanes to give Host-3 (9) 800 mg, in 46% yield.

Example 3

Synthesis of Host-4

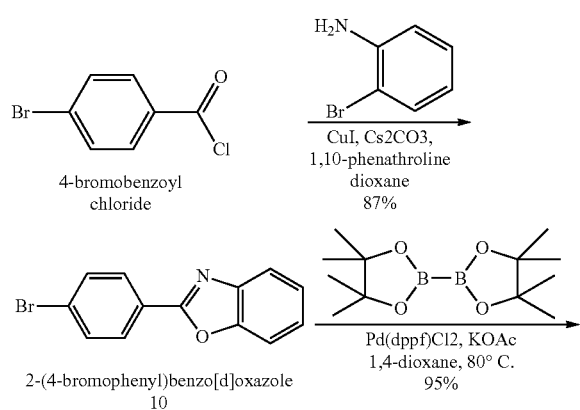

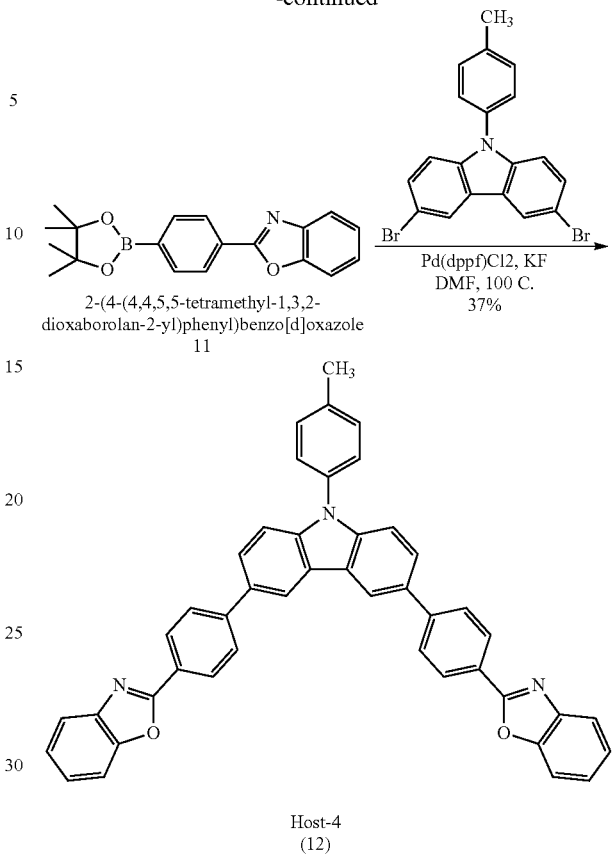

Host-4 (12)

2-(4-bromophenyl)benzo[d]oxazole (10)

A mixture of 4-bromobenzoylchloride (4.84 g, 22 mmol), 2-bromoaniline (3.8 g, 22 mmol), CuI (0.21 g, 1.1 mmol), $Cs_2CO_3$ (14.3 g, 44 mmol) and 1,10-phenathroline (0.398 g, 2.2 mmol) in anhydrous 1,4-dioxane (80 mL) was degassed and heated at about 125° C. under argon overnight. The mixture was cooled and poured into ethyl acetate (~200 mL) and filtered. The filtrate was absorbed on silica gel, purified by column chromatography (hexanes/ethyl acetate 4:1), and precipitated by hexanes to give a white solid (5.2 g, in 87% yield).

2-(4-(4,4,5,5-tetramethyl-1,3,2-dioxaborolan-2-yl) phenyl)benzo[d]oxazole (11)

A mixture of 10 (4.45 g, 16 mmol), bis(pinacolate)diborane (4.09 g, 16.1 mmol), anhydrous potassium acetate (3.14 g, 32 mmol) and $Pd(dppf)Cl_2$ (0.48 g, 0.66 mmol) in anhydrous 1,4-dioxane (80 mL) was degassed and heated at about 85° C. for about 48 hours under argon. After cooling to room temperature, the mixture was poured into ethyl acetate (~200 mL) and filtered. The filtrate was absorbed on silica gel and purified by column chromatography (hexanes/ethyl acetate, 4:1) to give a white solid (4.15 g, in 81% yield).

Host-4 (12)

A mixture of 3,6-dibromo-9-p-tolyl-9H-carbazole (2.62 g, 6.35 mmol), 10 (4.08 g, 12.7 mmol), $Pd(dppf)Cl_2$ and KF (2.21 g, 38 mmol) in DMF (100 mL) was heated at about 120°

Example 4

Synthesis of Host-5

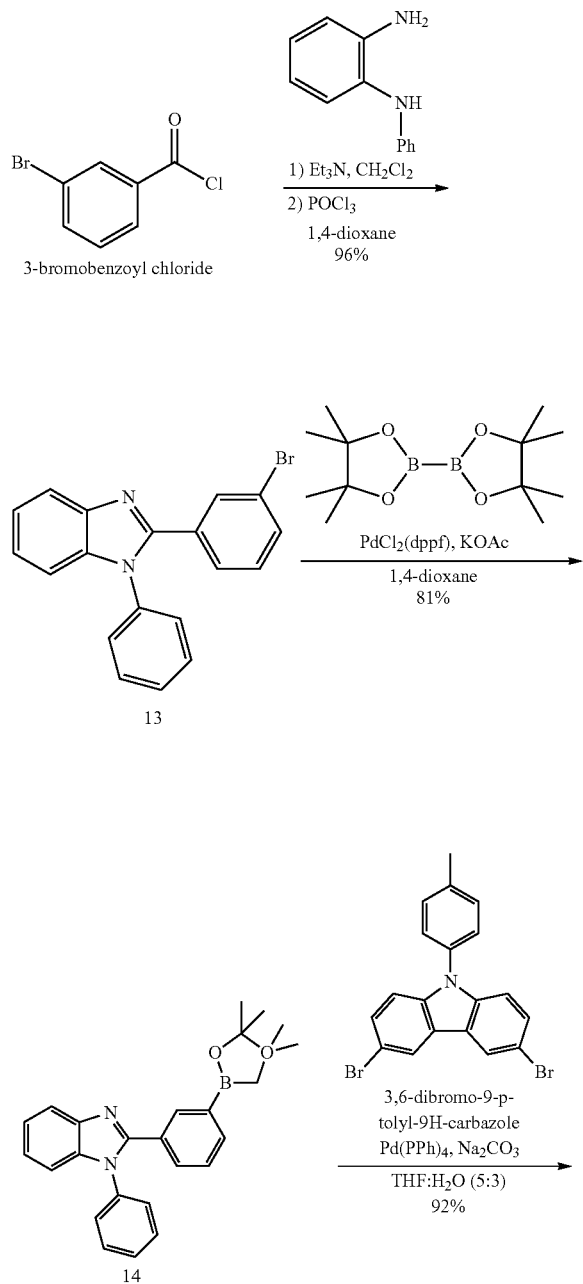

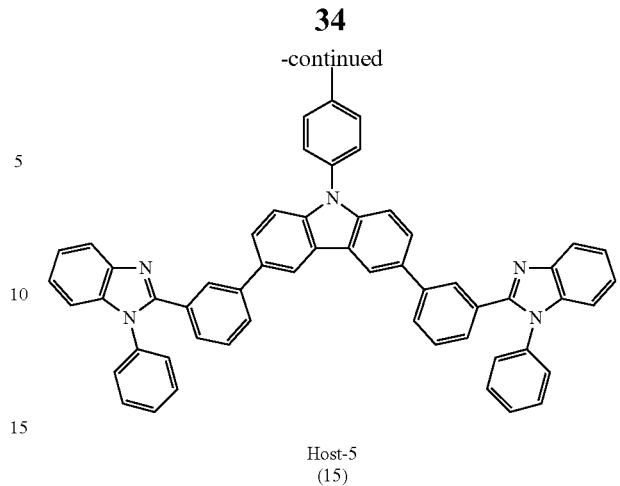

Host-5
(15)

2-(3-bromophenyl)-1-phenyl-1H-benzo[d]imidazole (13)

To a stirring solution of N-phenyl-o-phenylene-1,2-diamine (0.967 g, 5.25 mmol) in anhydrous $CH_2Cl_2$ (25 mL) was added 3-bromobenzoyl chloride (0.66 mL, 5 mmol) dropwise via syringe, followed by dropwise addition of $Et_3N$ (1.4 mL). Stirring was continued at room temperature until TLC ($SiO_2$, 4:1 hexanes-ethyl acetate) indicated consumption of the starting material (19 h). The reaction was then poured over water (~300 mL) and extracted with $CH_2Cl_2$ (3×~40 mL). The combined organics were washed with brine, dried over $MgSO_4$, filtered and concentrated. The crude intermediate was then dissolved in anhydrous 1,4-dioxane (~22 mL) and heated to about 115° C. Upon completely dissolving, phosphorus oxychloride (1.37 mL, 15 mmol) was added to the solution slowly via syringe and the reaction maintained at about 115° C. Upon completion (~2 h), the reaction was cooled to room temperature and poured over $CH_2Cl_2$ (~150 mL). The combined organics were then washed with saturated $NaHCO_3$, $H_2O$ and brine, dried over $MgSO_4$, filtered and concentrated in vacuo. The crude product was purified by flash chromatography ($SiO_2$, 4:1 hexanes-acetone) to afford 13 (1.68 g, 96%) as a light yellow solid.

1-phenyl-2-(3-(4,4,5,5-tetramethyl-1,3,2-dioxaborolan-2-yl)phenyl)-1H-benzo[d]imidazole (14)

A procedure from the literature (Ge, Z.; Hayakawa, T.; Ando, S.; Ueda, M.; Akiike, T.; Miyamoto, H.; Kajita, T.; Kakimoto, M. Chem. Mater. 2008, 20(7), 2532-2537) was modified as follows: a mixture of 13 (4.068 g, 11.65 mmol), bis(pinacolato)diboron (6.212 g, 24.46 mmol), [1,1'-bis(diphenylphosphino)-ferrocene]dichloropalladium(II) (0.571 g, 0.699 mmol), potassium acetate (3.430, 34.94 mmol) and 1,4-dioxane (80 mL) was degassed with argon for about 1 h while stirring. The reaction mixture was then maintained at about 80° C. with stirring under argon for about 17 h. Upon completion, the reaction was cooled to room temperature, filtered through a short silica gel plug (ca. ½ in.) and the filtrant washed copiously with EtOAc (~300 mL). The combined organics were then washed with sat. $NaHCO_3$, water and brine, dried over $MgSO_4$, filtered and concentrated in vacuo. Purification of the crude product via flash chromatography ($SiO_2$, 100% $CH_2Cl_2$ to 49:1 $CH_2Cl_2:CH_3OH$) and subsequent recrystallization from hexanes yielded boronic ester 14 (3.72 g, 81%) as an off-white, crystalline solid.

Host-5 (15)

A mixture of 14 (2.5 g, 6.309 mmol), 3,6-dibromo-9-p-tolyl-9H-carbazole (1.278 g, 3.077 mmol), tetrakis(triphenylphosphine)palladium(0) (0.178 g, 0.154 mmol), $Na_2CO_3$ (1.167 g, 11.01 mmol), $H_2O$ (10 mL) and THF (50 mL) was degassed with argon for about 25 min while stirring. The reaction mixture was then maintained at about 85° C. with stirring under argon for about 43 h. Upon completion, the reaction was cooled to room temperature and poured over EtOAc (~150 mL). The organics were then washed with sat. $NaHCO_3$, $H_2O$ and brine, dried over $MgSO_4$, filter and concentrated in vacuo. The crude product was purified via flash chromatography ($SiO_2$, 3:1 hexanes-acetone) to yield product Host-5 (15) (2.26 g, 92%) as an off-white powder.

Example 5

OLED Device Fabrication and Performance

Fabrication of red light-emitting device: the ITO coated glass substrates were cleaned by ultrasound in water, acetone, and consecutively in 2-propanol, baked at about 300° C. for about 30 min, followed by treatment with UV-Ozone for about 30 min. A layer of PEDOT: PSS (Baytron P purchased from H.C. Starck) was spin-coated at about 3000 rpm onto the pre-cleaned and UV-Ozone treated (ITO)-substrate and the substrate was baked at about 100° C. for about 30 min in a normal environment (air) followed by baking at about 200° C. for about 30 min inside a glove box and $N_2$ environment yielding a thickness of around 40 nm. In a glove-box hosted vacuum deposition system at a pressure of about $10^{-7}$ torr (1 torr=133.322 Pa), 4,4'-bis[N-(naphthyl)-N-phenyl-amino]biphenyl (NPB) was first deposited on top of PEDOT/PSS layer at deposition rate of about 0.1 nm/s, yielding a 30 nm thick film.

Figure 2:
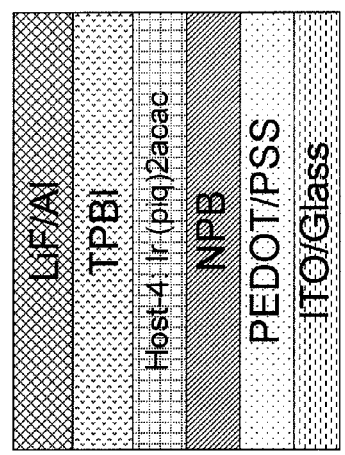
FIG. 2 shows an embodiment of an organic light-emitting device incorporating a compound of Formula 1.
Figure 5:
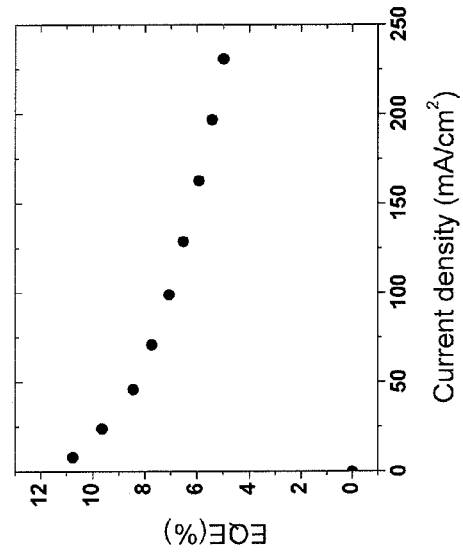
FIG. 5 is a graph depicting the External Quantum Efficiency (EQE) as a function of current density of an embodiment of an organic light-emitting device of FIG. 2.
Figure 6:
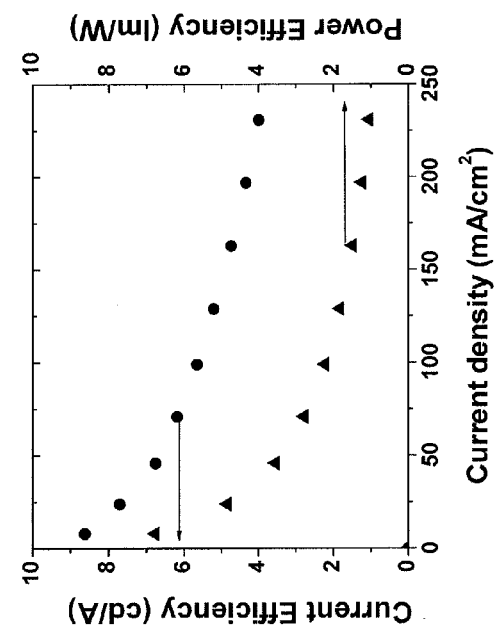
FIG. 6 is a graph depicting the luminous efficiency (cd/A) and power efficiency (lm/W) as a function of current density (mA/cm2) of an embodiment of an organic light-emitting device of FIG. 2.
Figure 4:
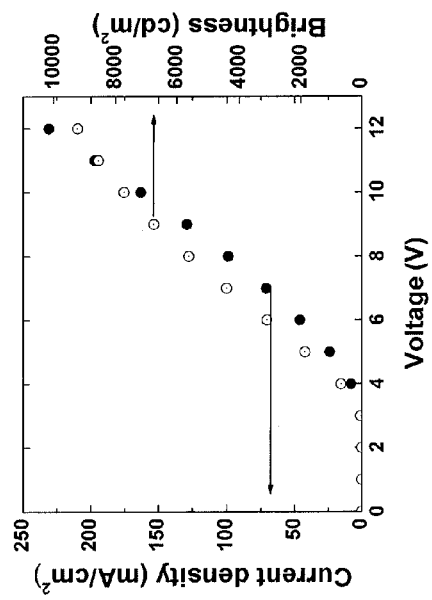
FIG. 4 is a graph depicting the current density (mA/cm2) and brightness (cd/m2) as a function of driving voltage of an embodiment of an organic light-emitting device of FIG. 2.
Figure 7:
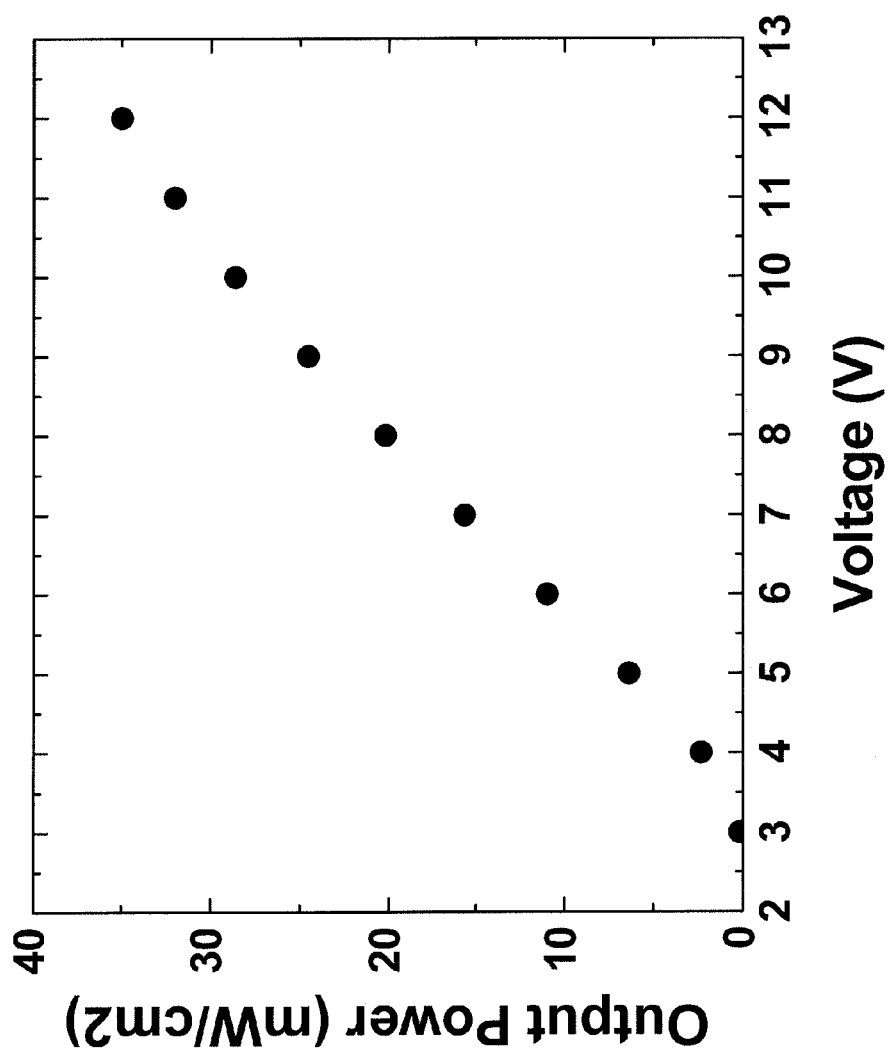
FIG. 7 shows a graph depicting the power output (mW/cm2) as a function of driving voltage of an embodiment of an organic light-emitting device of FIG. 2.

Then the Host-4 and red emitter bis(1-phenylisoquinoline)(acetylacetonate)iridium (III) ($Ir(piq)_2acac$) were co-deposited ($Ir(piq)_2acac$, 9 wt %) on top of NPB, yielding a 30 nm thick emissive layer, followed by deposition of 1,3,5-tris(N-phenylbenzimidizol-2-yl)benzene (TPBI) at deposition rate around 0.1 nm/s to form a 30 nm thick film. LiF (about 0.5 nm) and Al (about 120 nm) were then deposited successively at deposition rates of about 0.005 and about 0.3 nm/s, respectively. Each device has an active emissive area of about 1.6 $cm^2$. All spectra were measured with a Spectrascan spectroradiometer PR-670 (Photo Research, Inc., Chatsworth, Calif., USA); and 1-V-L characteristics were taken with a Keithley 2612 SourceMeter (Keithley Instruments, Inc., Cleveland, Ohio, USA) and PR-670. All device operation was performed inside a nitrogen-filled glove-box. An exemplary configuration of the device is shown in FIG. 2. FIGS. 3-7 show that the device is suitable as an OLED. FIG. 3 shows electroluminescence spectrum of the device. FIG. 4 shows current density and luminance as a function of the driving voltage of the device. FIG. 5 shows the external quantum efficiency (EQE) as a function of current density of the device. FIG. 6 shows current efficiency (cd/A) and power efficiency (lm/w) as a function of current density of the device. FIG. 7 shows the output power (mW/cm2) as a function of driving voltage of the device.

Example 6

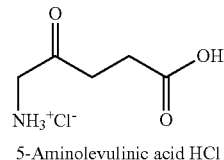

5-Aminolevulinic acid HCl

5-Aminolevulinic acid HCl (20% topical solution, available as LEVULAN® KERASTICK® from DUSA® Pharmaceuticals) is topically applied to individual lesions on a person suffering from actinic keratoses. About 14-18 hours after application, the treated lesions are illuminated with a red light emitting OLED device constructed as set forth in Example 5.

After the treatment, the number or severity of the lesions is anticipated to be reduced. The treatment is repeated as needed.

Example 7

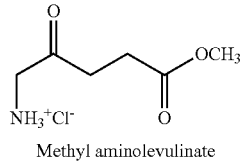

Methyl aminolevulinate

Methyl aminolevulinate (16.8% topical cream, available as METVIXIA® Cream from GALERMA LABORATORIES, Fort Worth, Tex., USA) is topically applied to individual lesions on a person suffering from actinic keratoses. The excess cream is removed with saline, and the lesions are illuminated with the red light emitting OLED constructed as set forth in Example 5.

Nitrile gloves are worn at all times during the handling of methyl aminolevulinate. After the treatment, it is anticipated that the number or severity of the lesions is reduced. The treatment is repeated as needed.

Example 8

Verteporphin is intravenously injected, over a period of about 10 minutes at a rate of about 3 mL/min, to a person suffering from age-related macular degeneration. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 $mg/m^2$ of body surface.

About 15 minutes after the start of the 10 minute infusion of verteporphin, the verteporphin is activated by illuminating the retina with a red light emitting OLED device as set forth in Example 5.

After treatment, the patient's vision is anticipated to be stabilized. The treatment is repeated as needed.

Example 9

Verteporphin is intravenously injected, over a period of about 10 minute at a rate of about 3 mL/min, to a person suffering from pathological myopia. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light emitting OLED device as set forth in Example 5.

After treatment, the patient's vision is anticipated to be stabilized. The treatment is repeated as needed.

Example 10

Verteporphin is intravenously injected, over a period of about 10 minutes at a rate of about 3 mL/min, to a person suffering from presumed ocular histoplasmosis. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light emitting OLED device (such as Device-A).

After treatment, the patient's vision is anticipated to be stabilized. The treatment is repeated as needed.

Example 11

Figure 8:
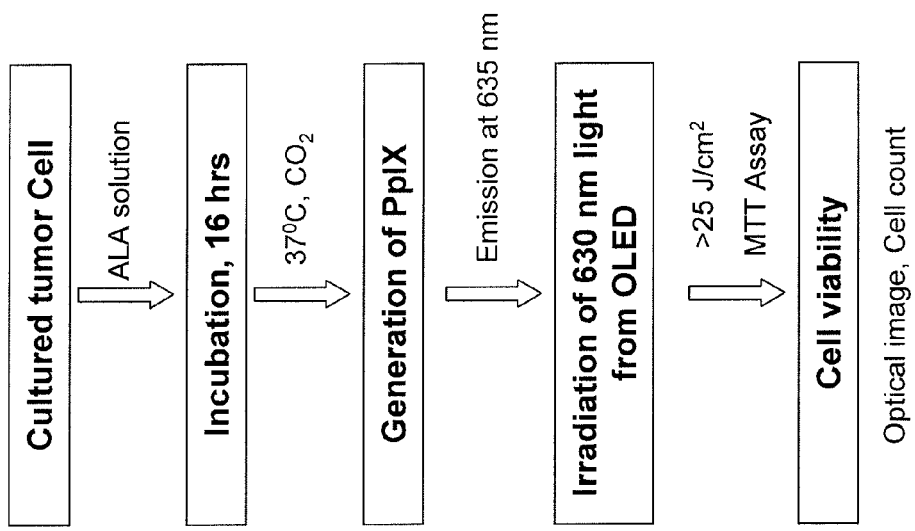
FIG. 8 is a schematic representation of ex-vivo efficacy study with the device output according to FIG. 7.

An efficacy study has been performed with a pro-drug named 5-aminolevulinic acid (ALA) and CHO-K1 (Chinese Hamster Ovarian Cancer, ATCC, CRL-2243) cell line. FIG. 8 exhibits the efficacy study scheme. Cells were cultured in a 96-well media (Hyclone F-12K medium and dulbeccdo phosphate buffer saline, DPBS) and incubated at 37° C. under $CO_2$ atmosphere for about 24 hrs and then was calibrated by cell counting with a standard cross area under optical microscope (Olympus IX-70) to establish a base reference number of cells of about 10,000 counts in 100 uL medium per well plate. ALA solutions (1.64 mg/mL in F-12K medium) introduced into same media as mentioned above and incubated for about 16 hrs at 37° C. under $CO_2$ atmosphere. While not being limited by theory, it is believed that in this process, ALA undergoes a biological transformation and is converted to protoporphyrin IX (PpIX). The generation of PpIX was confirmed by fluorescence emission at 635 nm.

Figure 9:
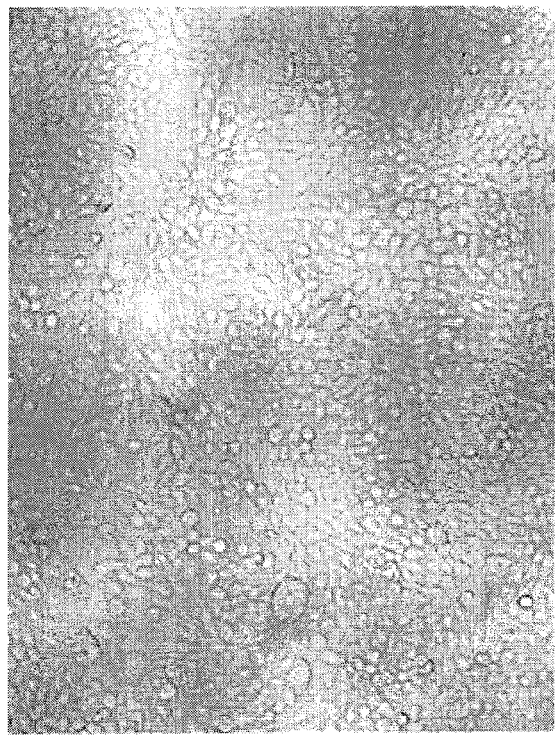
FIG. 9 shows the image of the cells before and after the light irradiation from OLED.
Figure 9:
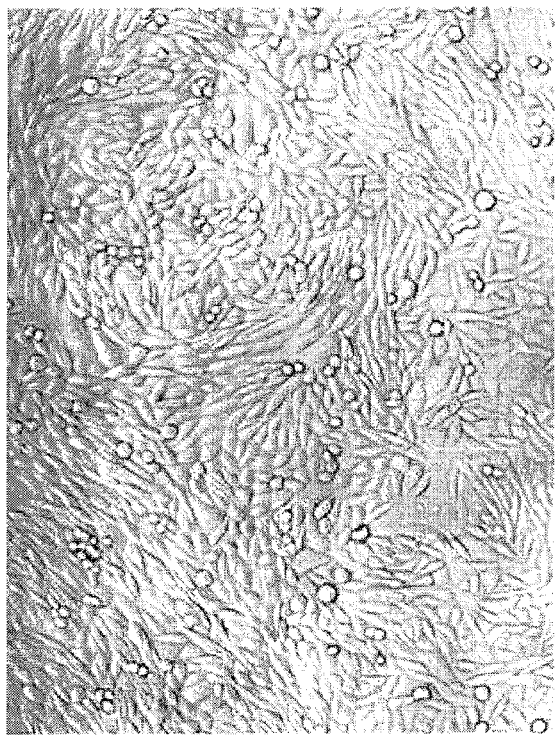

An OLED was constructed similar to that of Example 5. Red light (about 630 nm) was then irradiated from the OLED with a total dose of about 27 J/cm$^2$. While not being limited by theory, it is believed PpIX may absorb at about 630 nm light and may be excited to its singlet state followed by intersystem crossing to triplet state. Since the triplet state may have a longer lifetime, the triplet PpIX may interact with molecular oxygen and may generate singlet oxygen and other reactive oxygen species (ROS). These ROS may have a short lifetime and may have a diffusion length of only about several tens of nm. The ROS within their area may then undergo cytotoxic reaction with different cell components such as cell membrane, mitochondria, lisosome, golgy bodies, nucleus etc and may destroy them and ultimately tumor cell dies. Optical microscope (Olympus IX-70) images of the cells after 25 J/cm$^2$ red light irradiation shows (FIG. 9) that the healthy leafy type cells transforms to droplet type upon light irradiation indicating that a significant and irreversible cell death.

Figure 10:
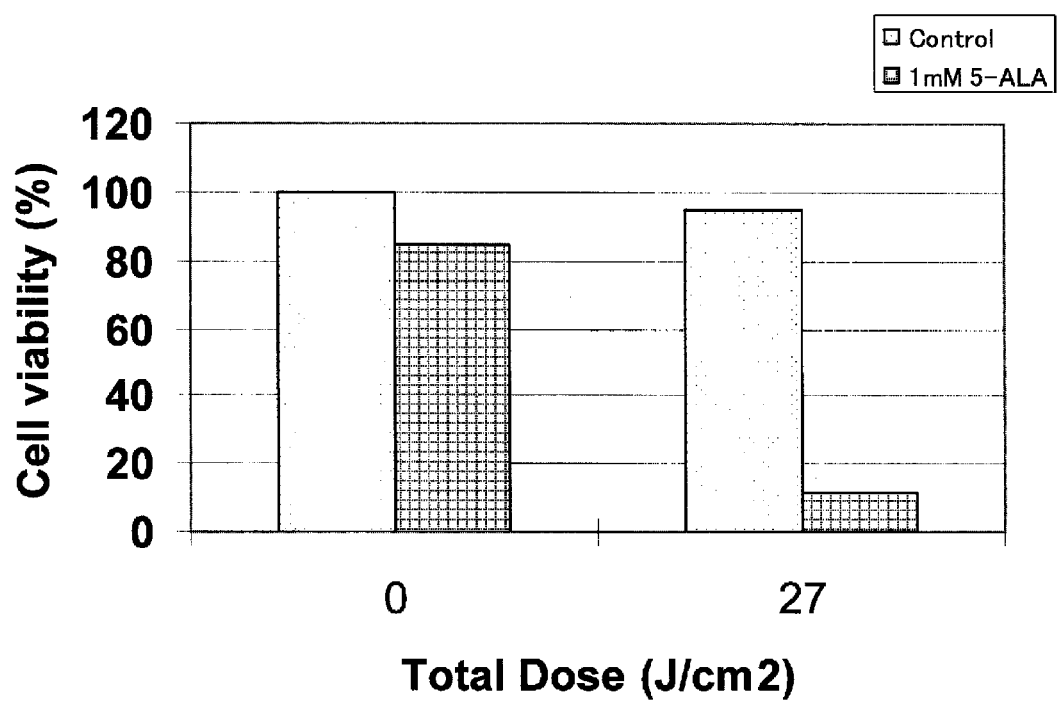
FIG. 10 shows cell viability (%) data after irradiating 27 J/cm2 with 1 mM 5-ALA solution.

Followed by light irradiation, 10 uL of MTT solution (Invitrogen, 3,(4,5-dimethylthiazol-2-yl)-2,5-diphenyl tetrazolium bromide, 5 mg/mL in DPBS) was added to each well including the control well and shaken well to mix precisely. The wells were incubated (37° C., 5% $CO_2$) for 1.5 hrs to generate purple crystal. Then 100 uL MTT solubilization solution were added to each well and incubated (37° C., 5% $CO_2$) for 16 hrs to dissolve purple crystals. Finally the absorbance of the cells ar 570 nm with a reference wavelength at 690 nm were recorded by a microplate reader (BioTeK MQX-200) in order to estimate cell viability (%). Cell viability results are shown in FIG. 10. It is clearly shown that almost 90% cell destroyed with 1 mM of ALA concentration compared with reference. It was found that at least 1 mM concentration of ALA will be required at the dose of 27 J/cm$^2$. The reference cells were irradiated with same dose of light but without ALA. For a better comparison identical cells were kept at normal environment without light irradiation and compared with reference.

Although the claims have been described in the context of some specific embodiments and examples, it will be understood by those skilled in the art that the scope of the claims extend beyond the specifically disclosed embodiments to other alternative embodiments and/or uses of the invention and obvious modifications and equivalents thereof.

What is claimed is:

1. A light-emitting device for use in phototherapy comprising:
    a light-emitting layer comprising a compound selected from the groups consisting of:

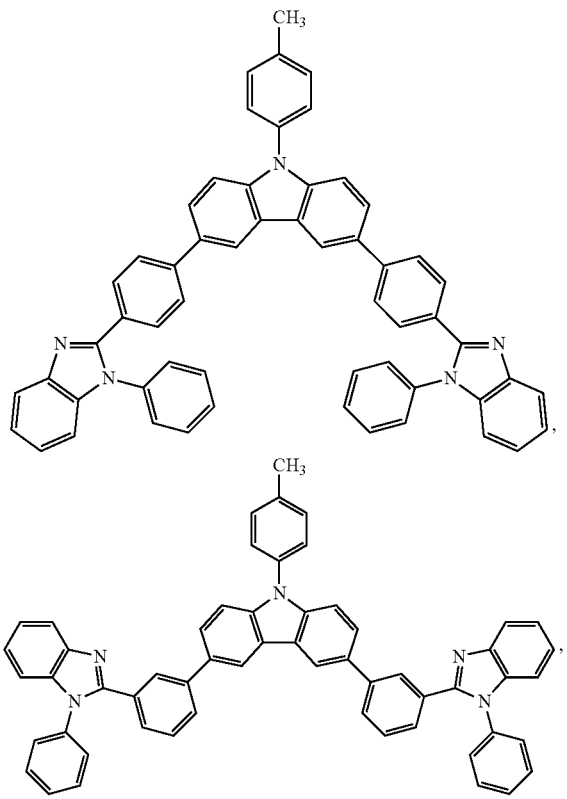

-continued
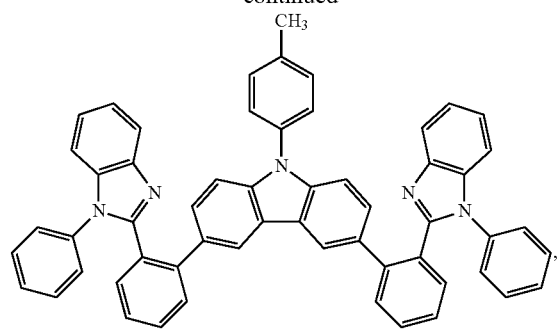
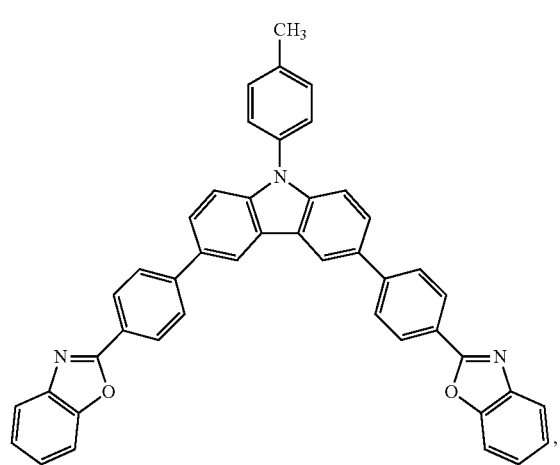
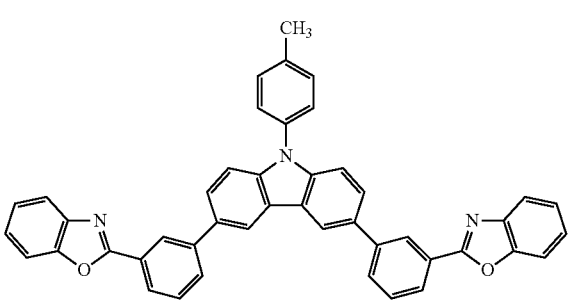
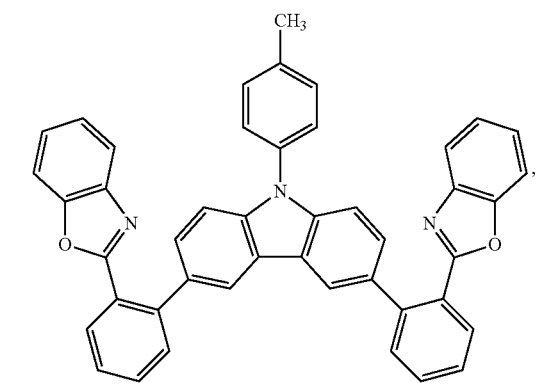
-continued
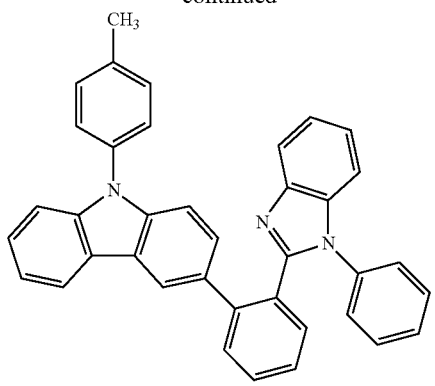
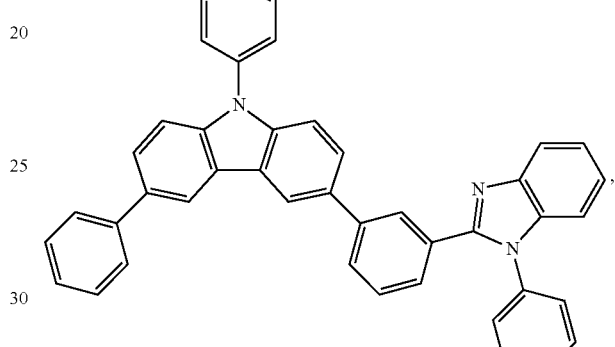
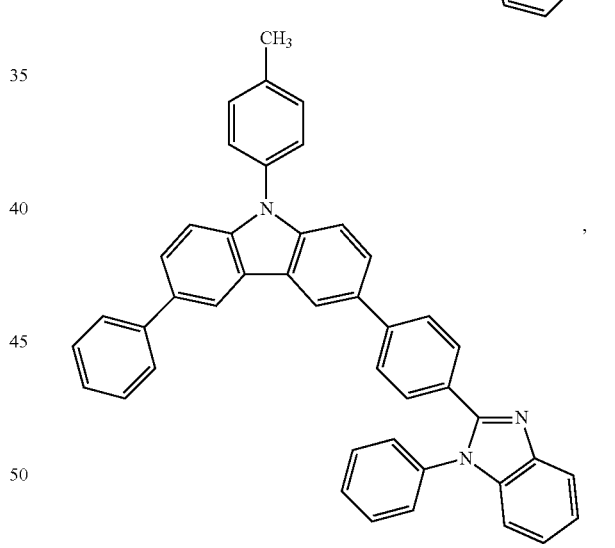
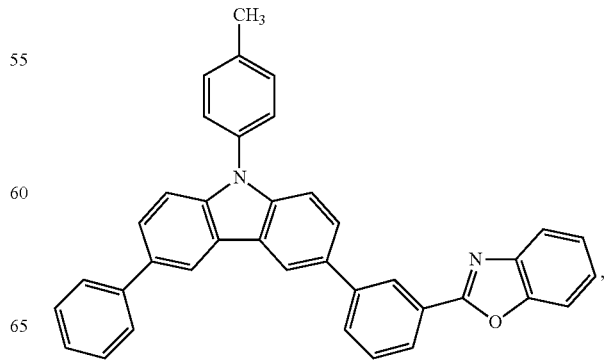

-continued

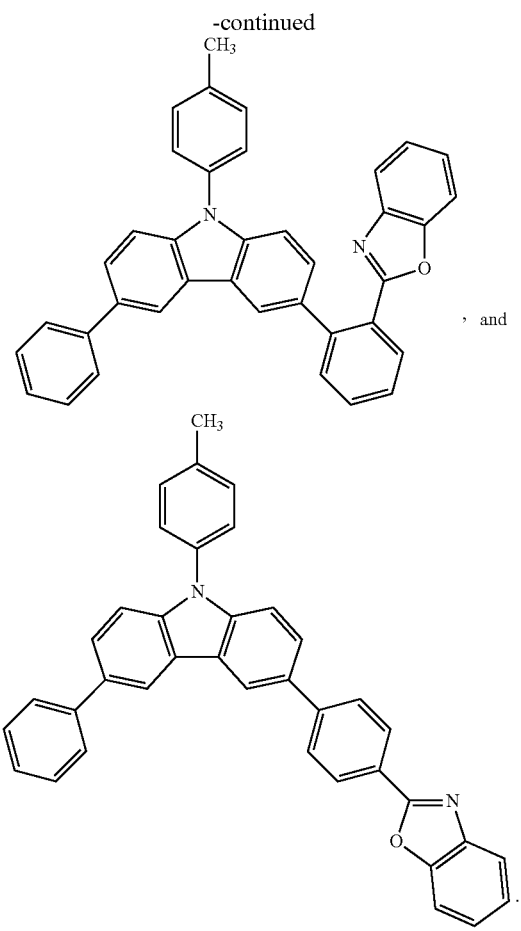

, and

2. The device of claim 1, wherein the device is configured to emit light of a wavelength that can activate at least a portion of a photosensitive compound which has been administered to a tissue of a mammal; and wherein the device further comprises a dosage component configured to provide a sufficient amount of light to activate a sufficient portion of the photosensitive compound to provide a therapeutic effect for treating a disease.

3. A phototherapy system comprising:
a device according to claim 1; and
a wound dressing.

4. A method of carrying out phototherapy comprising:
exposing at least a portion of a tissue of a mammal to light from a device of claim 1.

5. The method of claim 4, further comprising administering a photosensitive compound to the tissue, and wherein at least a portion of the photosensitive compound is activated by exposing the portion of the tissue to light from the device.

6. A method of treating a disease, comprising:
administering a photosensitive compound to a tissue of a mammal in need thereof;
exposing at least a portion of the tissue to light from a device of claim 1; and
wherein at least a portion of the photosensitive compound is activated by at least a portion of the light from the device to which the tissue is exposed, to thereby treat the disease.

7. The method of claim 6, wherein activating the photosensitive compound produces singlet oxygen.

8. The method of claim 6, wherein the photosensitive compound is 5-aminolevulinic acid, verteporfin, zinc phthalocyanine, or pharmaceutically acceptable salts thereof.

9. The method of claim 6, wherein the disease is cancer.

10. The method of claim 6, wherein the disease is a microbial infection.

11. The method of claim 6, wherein the disease is a skin condition.

12. The method of claim 6, wherein the disease is an eye condition.

13. A phototherapy system comprising:
a device according to claim 1; and
a photosensitive compound;
wherein the photosensitive compound is suitable for administration to a tissue of a mammal in need of phototherapy; and
wherein the device is configured to emit light of a wavelength which can activate at least a portion of the photosensitive compound when it is in the tissue.

* * * * *